(12) United States Patent
Neidle et al.

(10) Patent No.: US 9,493,460 B2
(45) Date of Patent: Nov. 15, 2016

(54) DIIMIDE COMPOUNDS

(71) Applicant: UCL BUSINESS PLC, London (GB)

(72) Inventors: Stephen Neidle, Herts (GB); Stephan A. Ohnmacht, Cote d'Or (FR); Mekala Gunaratnam, London (GB); Aaron Grainger Dale, Wrexham (GB); Marialuisa Micco, Rimini (IT); Gavin William Collie, Aberdeenshire (GB)

(73) Assignee: UCL BUSINESS PLC, London (GB)

( * ) Notice: Subject to any disclaimer, the term of this patent is extended or adjusted under 35 U.S.C. 154(b) by 8 days.

(21) Appl. No.: 13/801,491

(22) Filed: Mar. 13, 2013

(65) Prior Publication Data

US 2014/0275062 A1    Sep. 18, 2014

(51) Int. Cl.
C07D 471/08    (2006.01)
C07D 471/06    (2006.01)

(52) U.S. Cl.
CPC .................. *C07D 471/06* (2013.01)

(58) Field of Classification Search
CPC ........................ C07D 471/04; C07D 471/08
USPC .................. 546/76; 544/125; 514/232.8, 288
See application file for complete search history.

(56) References Cited

U.S. PATENT DOCUMENTS

2010/0311739 A1*  12/2010  Gunaratnam et al. ..... 514/232.8

FOREIGN PATENT DOCUMENTS

WO    WO-2009/068916 A1    6/2009

OTHER PUBLICATIONS

Mitchell et al. "Downregulation of Androgen Receptor Transcription by Promoter G-Quadruplex Stablization as a Potential Alternative Treatment for Castrate-Resistant Prostate Cancer" Biochemistry, Jan. 30, 2013, vol. 52, pp. 1429-1436.*
PubChem Compound Database, Jan. 3, 2013, CID #70680052, http://pubchem.ncbi.nlm.nih.gov/compound/70680052, pp. 1-13.*
STN Registry, Mar. 3, 2013, RN 1422376-60-0 and RN 1422376-59-7.*
Lu, X. et al. "Near-IR Core-Substituted Naphthalenediimide Fluorescent Chemosensors for Zinc Ions: Ligand Effects on PET and ICT Channels" *Chemistry: a European Journal*, Jul. 26, 2010, 16(28):8355-8364.

Chaignon, F. et al. "Very large acceleration of the photoinduced electron transfer in a Ru(bpy)₃- naphthalene bisimide dyad bridged on the naphthyl core" *Chemical Communications*, 2007, 1:64-66.
Gunaratnam, M. et al. "Targeting pancreatic cancer with a G-quadruplex ligand" *Bioorganic & Medicinal Chemistry*, Dec. 1, 2011, 19(23):7151-7157.
Hampel, S.M. et al. "Tetrasubstituted naphthalene diimide ligands with selectivity for telomeric G-quadruplexes and cancer cells" *Bioorganic & Medicinal Chemistry Letters*, Nov. 15, 2010, 20(22):6459-6463.
Gunaratnam, M. et al. "Targeting Human Gastrointestinal Stromal Tumor Cells with a Quadruplex-Binding Small Molecule" *Journal of Medicinal Chemistry*, Jun. 25, 2009, 52(12):3774-3783.
Collie, G.W. et al. "Structural Basis for Telomeric G-Quadruplex Targeting by Naphthalene Diimide Ligands" *Journal of the American Chemical Society*, Feb. 8, 2012, 134(5):2723-2731.
Micco, M. et al. "Structure-guided optimization of tetra-substituted naphthalene diimide G- quadruplex compounds leads to enhanced potency in cancer cell lines" Poster Presented at the American Association for Cancer Research meeting, Apr. 1, 2012, Chicago.
Micco, Marialuisa, et al. "Structure-based design and evaluation of naphthalene diimide G-quadruplex ligands as telomere targeting agents in pancreatic cancer cells." *Journal of medicinal chemistry* 56.7 (2013): 2959-2974.
Ohnmacht et al., "A G-quadruplex-binding Compound Showing Anti-tumour Activity in an in vivo Model for Pancreatic Cancer", *Nature Scientific Reports*, 5:11385, Jun. 16, 2015.

* cited by examiner

*Primary Examiner* — Kendra D Carter
(74) *Attorney, Agent, or Firm* — Saliwanchik, Lloyd & Eisenschenk

(57) ABSTRACT

The invention relates to novel compounds which are naphthalene diimides of general formula (I):

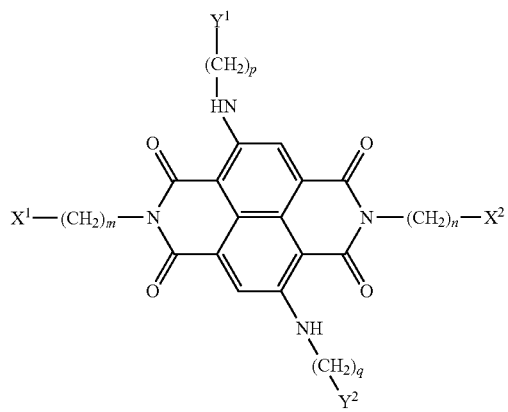

(I)

The compounds are used in therapy, particularly in cancer treatment.

17 Claims, 8 Drawing Sheets

SEQUENCE LISTING

```
<160> NUMBER OF SEQ ID NOS: 5

<210> SEQ ID NO 1
<211> LENGTH: 10
<212> TYPE: DNA
<213> ORGANISM: Homo sapiens

<400> SEQUENCE: 1 dgggttaggg                                                          10

<210> SEQ ID NO 2
<211> LENGTH: 11
<212> TYPE: DNA
<213> ORGANISM: Homo sapiens

<400> SEQUENCE: 2
dtatagctat a                                                        11

<210> SEQ ID NO 3
<211> LENGTH: 10
<212> TYPE: DNA
<213> ORGANISM: Homo sapiens

<400> SEQUENCE: 3
tatagctata                                                          10

<210> SEQ ID NO 4
<211> LENGTH: 21
<212> TYPE: DNA
<213> ORGANISM: Homo sapiens

<400> SEQUENCE: 4
gggccaaagg gaaggggtgg g                                             21

<210> SEQ ID NO 5
<211> LENGTH: 21
```

```
<212> TYPE: DNA
<213> ORGANISM: Homo sapiens

<400> SEQUENCE: 5
gggcgggcca aagggaaggg g                                         21
```

DIIMIDE COMPOUNDS

FIELD OF THE INVENTION

The present invention relates to novel compounds which are naphthalene diimides, more particularly tetra-substituted naphthalene diimides. The invention also concerns pharmaceutical compositions comprising the novel compounds and their use in therapy, particularly in cancer treatment.

BACKGROUND

The concept that small molecules can sequester the single-stranded overhang of human telomeric DNA into higher-order quadruplex DNA structures has been validated by a number of studies. It has also been shown that the resulting stabilized quadruplex-ligand complexes can interfere with the processivity of the reverse transcriptase telomerase enzyme complex and so inhibit the ability of this enzyme to maintain telomere integrity in the majority of cancer cell types, where it is up-regulated. The success of this approach to selectively interfering with cancer cell viability has been demonstrated for several classes of quadruplex-binding molecules in cells and in tumor xenograft experiments. Quadruplex targeting has also been shown to provoke a DNA damage response in cells Tetra-substituted naphthalene diimide (ND) derivatives with four side-chains, each terminating in a positively-charged group, have previously been shown to be potent stabilizers of human telomeric and various promoter quadruplexes. They are also potent inhibitors of the growth of human cancer cell lines and of the action of the telomerase enzyme. An initial lead ND compound with four positively-charged N-methyl-piperazine groups has previously shown antitumor activity in a human Mia-PaCa2 pancreatic carcinoma.

We have described, in our previous patent application published as WO2009/068916, naphthalene diimide compounds and their use in cancer treatment. Compounds with two N-methylpiperazine side chains were not disclosed.

In view of the prior art, there is a need to provide improved anti-cancer agents. In particular, there is a need to provide further naphthalene diimide derivatives which have improved G-quadruplex binding ability and anti-cancer effects.

BRIEF SUMMARY

In a first aspect of the invention, there is provided a compound of general formula (I) or a pharmaceutically acceptable salt or prodrug thereof

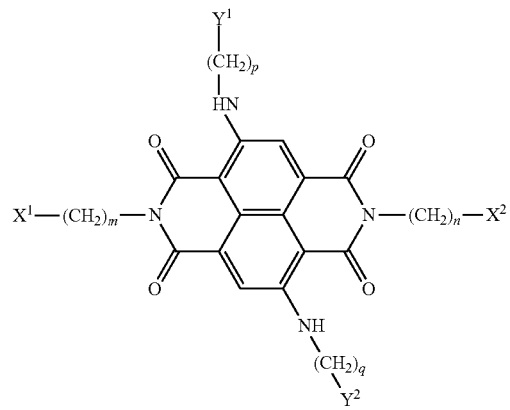

wherein m, n, p and q are each independently selected from integers 1, 2, 3 and 4;

wherein two of groups $X^1$, $X^2$, $Y^1$ and $Y^2$ are N-methyl piperazine, wherein two of groups $X^1$, $X^2$, $Y^1$ and $Y^2$ are independently selected from morpholino, furan, tetrahydrofuran, tetrahydropyran, pyrrolidine, piperidine, pyranose and $OR^1$, wherein $R^1$ is $C_{1-4}$ alkyl.

In a second aspect of the invention, there is provided a method for the treatment or prophylaxis of cancer comprising administering to a subject a compound of general formula (I), or a salt, solvate or prodrug thereof.

In a third aspect of the invention, there is provided a method of use a compound of general formula (I) or a pharmaceutically acceptable salt or prodrug thereof in the preparation of a pharmaceutical composition.

In a fourth aspect of the invention, there is provided a pharmaceutical composition comprising a compound of general formula (I) or a pharmaceutically acceptable salt or prodrug thereof.

DETAILED DESCRIPTION

The present invention is based on the results of a structure-based design study in which the four positive charges of compound 4 of the prior art (shown below) have been modified by substituting N-methyl-piperazine groups on two of the four side-arms of the ND core with more weakly basic groups, with the aim of improving the pharmacological properties of the ND series without compromising quadruplex interaction. It is believed that some diminution in the highly cationic nature of these naphthalene diimide compounds improves cellular uptake and potential tumour distribution properties, while retaining quadruplex affinity.

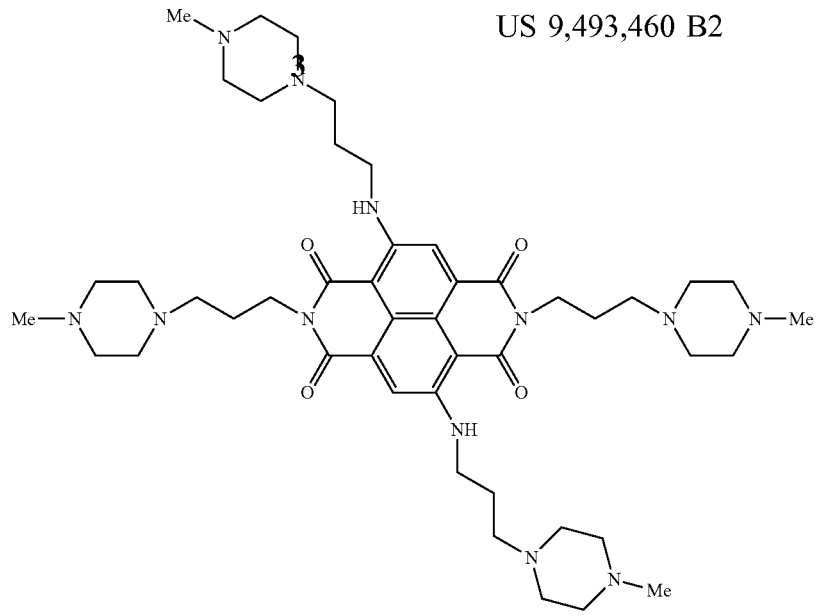

It is preferred at least one of the $X^1$, $X^2$, $Y^1$ and $Y^2$ groups is a morpholino group. This is preferred, not only because a morpholino group slightly reduces the overall molecular weight of the compounds, compared to all four of the $X^1$, $X^2$, $Y^1$ and $Y^2$ groups being N-methyl-piperazine but more importantly because it is significantly less basic than the protonated N-methyl-piperazine ring, with a pK of 8.5 compared to that for the latter, of 9.2.

It is surprising that the combination of two of $X^1$, $X^2$, $Y^1$ and $Y^2$ groups being N-methyl-piperazine and at least one of $X^1$, $X^2$, $Y^1$ and $Y^2$ groups being morpholino leads to compounds with activity, because as shown in WO2009/068916, compounds with morpholino groups are expected to be substantially inactive.

Other preferred compounds may have non-charged groups for two of the $X^1$, $X^2$, $Y^1$ and $Y^2$ groups, preferably methoxy, furan, tetrahydrofuran or tetrahydropyran.

Typically, the two N-methyl-piperazine groups are in the $X^1$ and $X^2$ positions. This is preferred as the shape of the compounds are appropriate for quadruplex binding. A particularly preferred compound has two morpholino groups for groups $X^1$, $X^2$, $Y^1$ and $Y^2$, along with the two N-methyl-piperazine groups. Preferably $X^1$ and $X^2$ are N-methyl-piperazine groups and $Y^1$ and $Y^2$ are both morpholino groups. However, structural isomers of these compounds are also included in the scope of the invention.

Preferably, the value of m, n, p and q are each independently selected from integers 1, 2 and 3.

When $Y^1$ and $Y^2$ are both morpholino groups, p and q are preferably 2. Such compounds show superior selectivity for quadruplex over duplex DNA.

The present invention also provides the use of a compound of formula (I), or a salt, solvate or pro-drug thereof, substantially as described herein before, in the manufacture of a medicament for the prophylaxis or treatment of cancer.

The compounds of the present invention may be present in the form of pharmaceutical acceptable salts. Pharmaceutically acceptable salts of the acidic or basic compounds of the invention can of course be made by conventional procedures, such as by reacting the free base or acid with at least a stoichiometric amount of the desired salt-forming acid or base.

Pharmaceutically acceptable salts of the acidic compounds of the invention include salts with inorganic cations such as sodium, potassium, calcium, magnesium, zinc, and ammonium, and salts with organic bases. Suitable organic bases include N-methyl-D-glucamine, arginine, benzathine, diolamine, olamine, procaine and tromethamine.

Pharmaceutically acceptable salts of the basic compounds of the invention include salts derived from organic or inorganic acids. Suitable anions include acetate, adipate, besylate, bromide, camsylate, chloride, citrate, edisylate, estolate, fumarate, gluceptate, gluconate, glucuronate, hippurate, hyclate, hydrobromide, hydrochloride, iodide, isethionate, lactate, lactobionate, maleate, mesylate, methylbromide, methylsulfate, napsylate, nitrate, oleate, pamoate, phosphate, polygalacturonate, stearate, succinate, sulfate, sulfosalicylate, tannate, tartrate, terephthalate, tosylate and triethiodide.

The compounds of general formula (I) may be prodrugs, that is compounds which are converted into the active drug at an appropriate target location in the human or animal body. For instance, when any or all of the groups $X^1$-$X^4$ are amines, $NR^3R^4$, the amine may be oxidised to form an N-oxide, $N^+(\!-\!O^-) R^3R^4$, which is a prodrug and can be bioreduced in hypoxic tissue.

Pro-drug forms of the pharmacologically-active compounds of the invention may be compounds according to formula (I) having an acid group which is esterified or amidated. Included in such esterified acid groups are groups of the form $-\!C(O)OR^a$, wherein $R^a$ is $C_{1\text{-}6}$ alkyl, phenyl, substituted phenyl, benzyl, substituted benzyl, or one of the following:

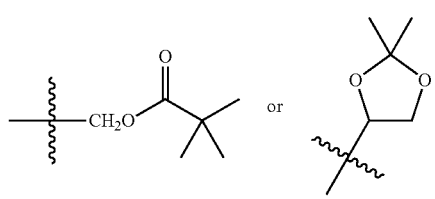

Amidated acid groups include groups of the formula $-\!CONR^bR^c$, wherein $R^b$ is H, $C_{1\text{-}5}$ alkyl, phenyl, substituted phenyl, benzyl, or substituted benzyl, and $R^c$ is $-\!OH$ or one of the groups just recited for $R^b$.

Compounds of formula (I) having an amino group may be derivatised with a ketone or an aldehyde such as formaldehyde to form a Mannich base. This will hydrolyse with first order kinetics in aqueous solution.

Pharmaceutical compositions of the present invention preferably comprise a compound of general formula (I), or a pharmaceutically acceptable salt or prodrug thereof and a pharmaceutically acceptable excipient.

It is anticipated that the compounds of the invention can be administered to a patient in need thereof by oral or parenteral routes, including intravenous, intramuscular, intraperitoneal, subcutaneous, rectal and topical administration, and inhalation.

For oral administration, the compounds of the invention will generally be provided in the form of tablets or capsules or as an aqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate and lactose. Corn starch and alginic acid are suitable disintegrating agents. Binding agents may include starch and gelatine. The lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatine capsules in which the active ingredient is mixed with a solid diluent and soft gelatine capsules wherein the active ingredient is mixed with water or an oil such as peanut oil, liquid paraffin or olive oil.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The novel compounds of this invention may be used in a method of medical treatment, particularly in the treatment of prostate cancer, lung cancer, renal cancer, pancreatic cancer, breast cancer or melanoma.

In the treatment, a therapeutically effective amount of a compound of general formula (I), or a salt, solvate or prodrug thereof, is administered to a patient in need thereof.

Preferred compounds are 3a-3h as shown below (compound 4 belongs to the prior art).

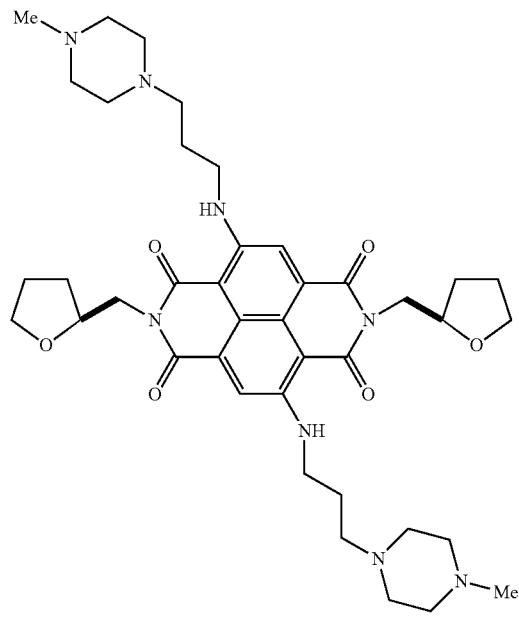

3a

-continued
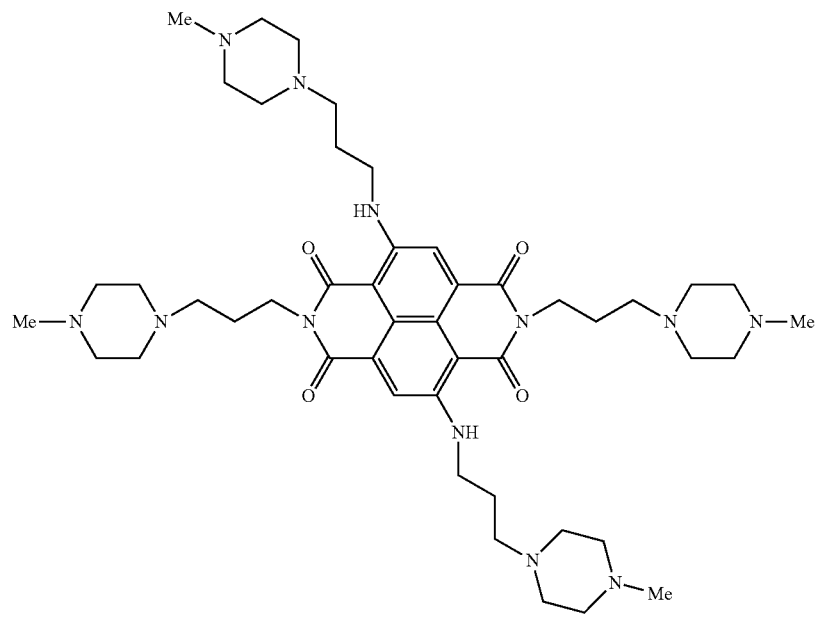
4
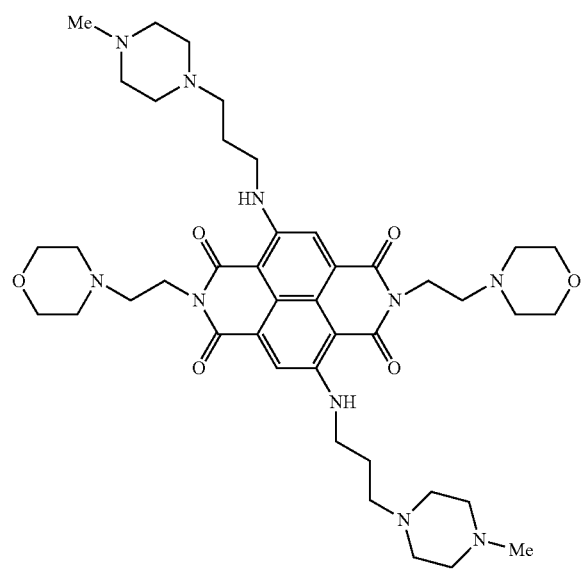
3f
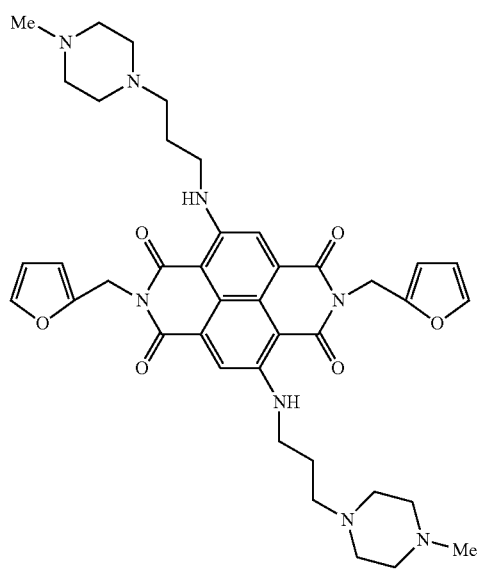
3b

-continued
3c
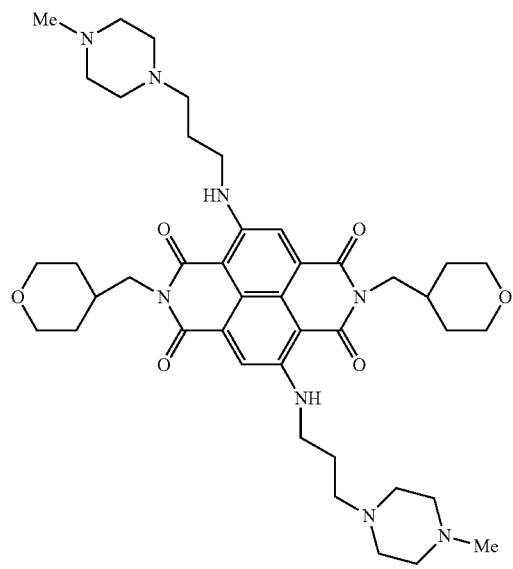
3g
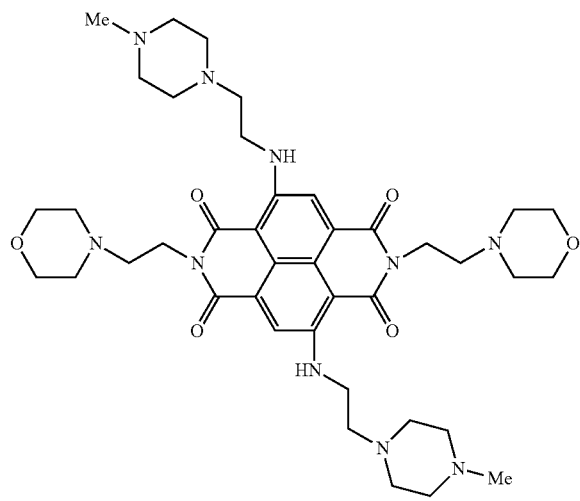
3d
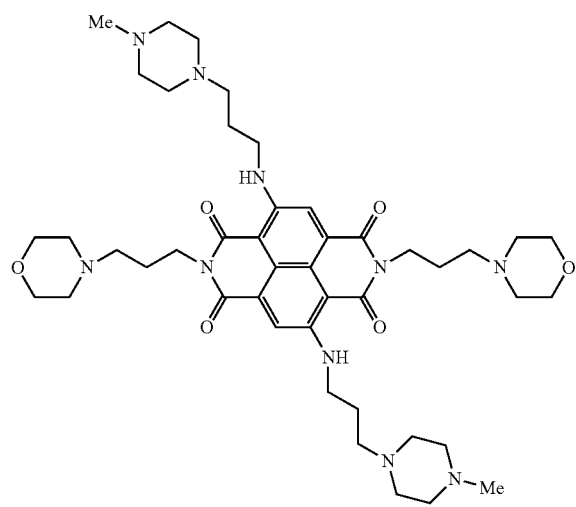 [SMILES: CN1CCN(CCCNc2cc3c4c(c(NCCCN5CCN(C)CC5)cc5c4c2C(=O)N(CCCN2CCOCC2)C5=O)C(=O)N(CCCN2CCOCC2)C3=O)CC1]
3e
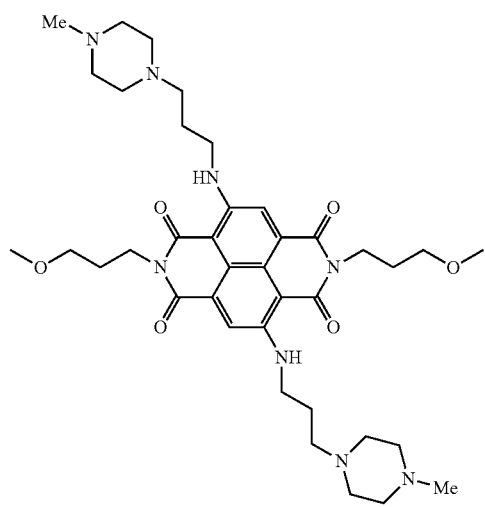
3h
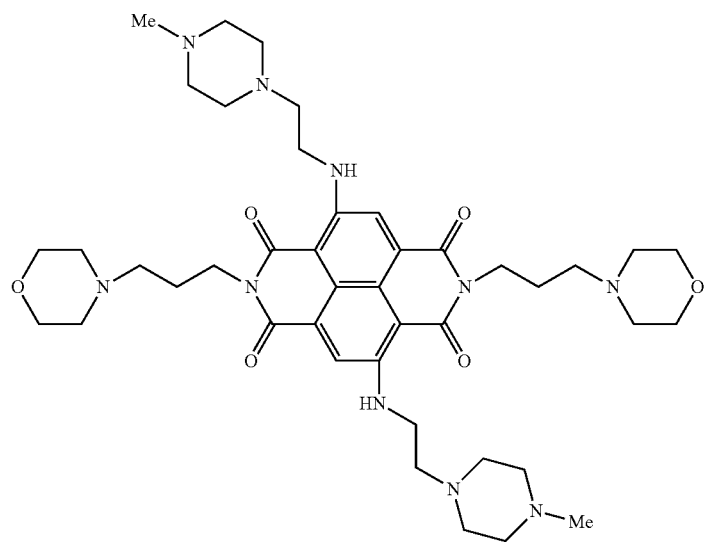

Compounds 3a-h can be synthesized according to the Scheme below, with the dibromo precursor 1 obtained by a published procedure[4], using commercially available amines.

The methodology is closely similar to that previously reported. A representative synthesis is outlined in Scheme (I) below. The tetrahydrofuran derivatives are racemic.

Scheme (I)

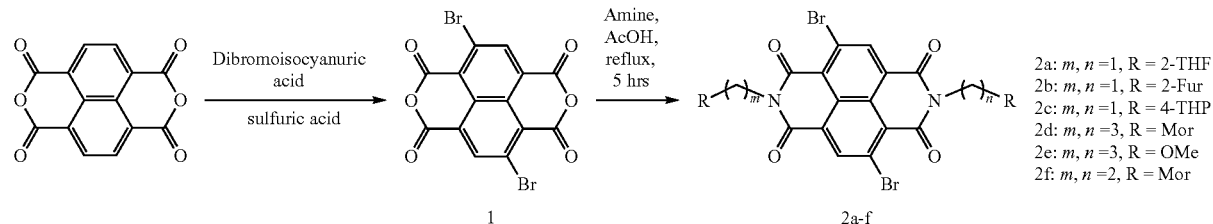

2a: $m, n = 1$, R = 2-THF
2b: $m, n = 1$, R = 2-Fur
2c: $m, n = 1$, R = 4-THP
2d: $m, n = 3$, R = Mor
2e: $m, n = 3$, R = OMe
2f: $m, n = 2$, R = Mor

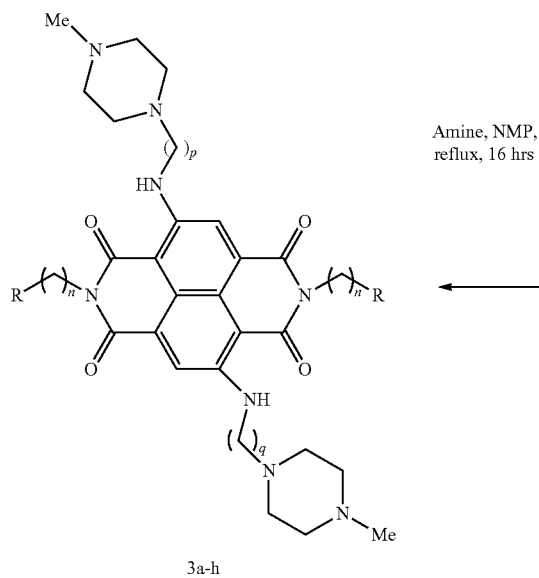

3a: $m, n = 1, p, q = 3$, R = 2-THF
3b: $m, n = 1, p, q = 3$, R = 2-Fur
3c: $m, n = 1, p, q = 3$, R = 4-THP
3d: $m, n = 3, p, q = 3$, R = Mor
3e: $m, n = 3, p, q = 3$, R = OMe
3f: $m, n = 2, p, q = 3$, R = Mor
3g: $m, n = 2, p, q = 2$, R = Mor
3h: $m, n = 3, p, q = 2$, R = Mor

Other preferred compounds include structural isomers of these compounds as shown in Scheme (II)

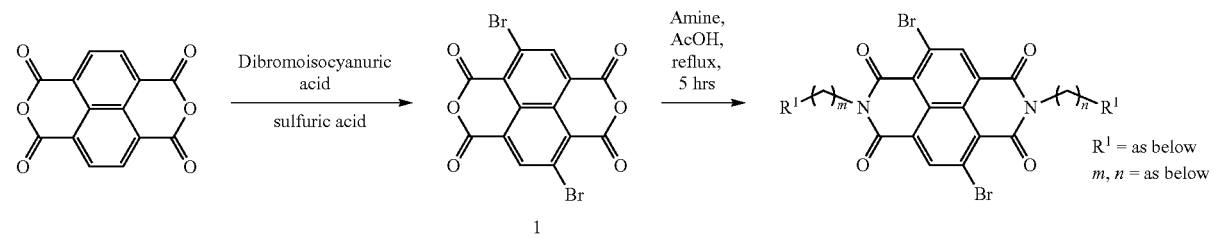

$R^1$ = as below
$m, n$ = as below

-continued
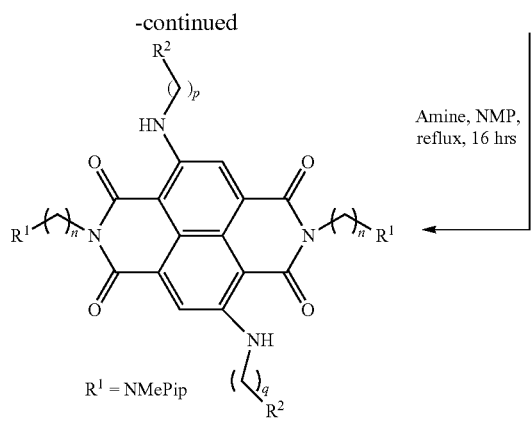
SKM22: m, n = 3, p, q = 3, R² = OMe
SKM29: m, n = 3, p, q = 3, R² = Mor
SKM36: m, n = 2, p, q = 3, R² = Mor
SKM38: m, n = 3, p, q = 1, R² = 2-THF
SKM52: m, n = 3, p, q = 1, R² = 4-THP
Note: SKM38 is racemic, so is compound 3a, its isomer.
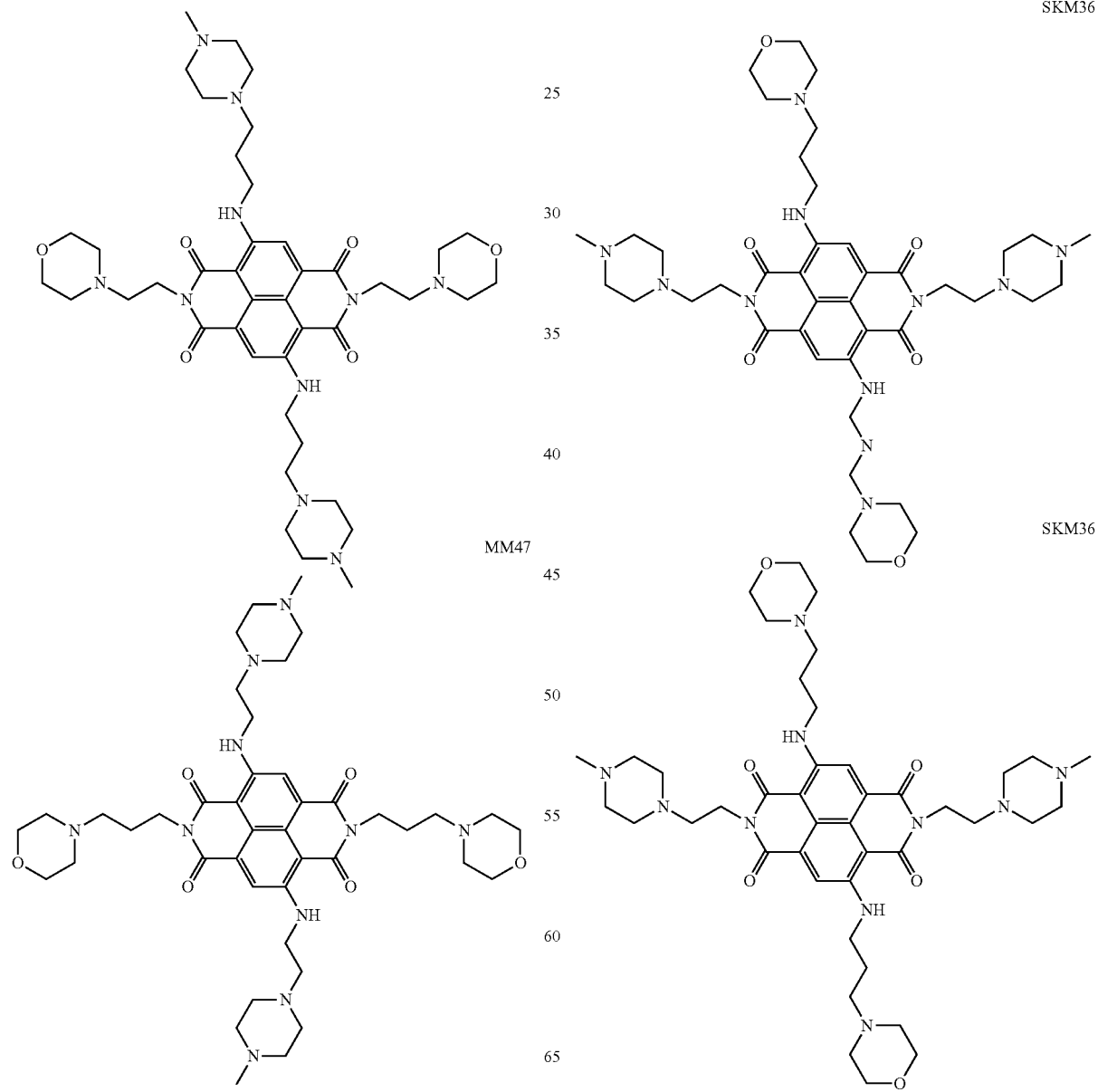

-continued
MM41
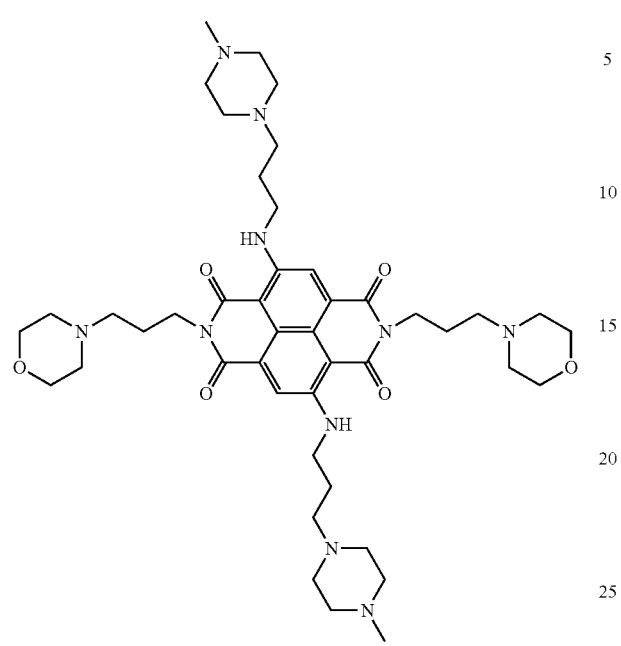
MM10
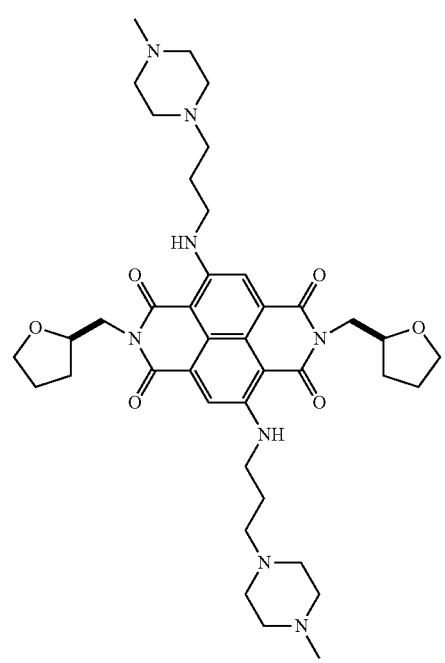
SKM29
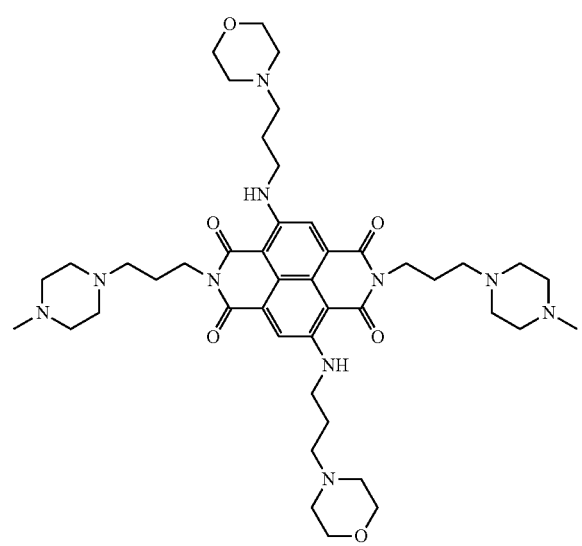
SKM52
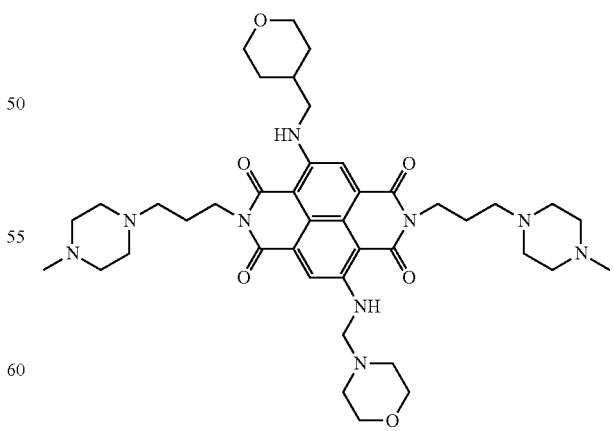

MM33

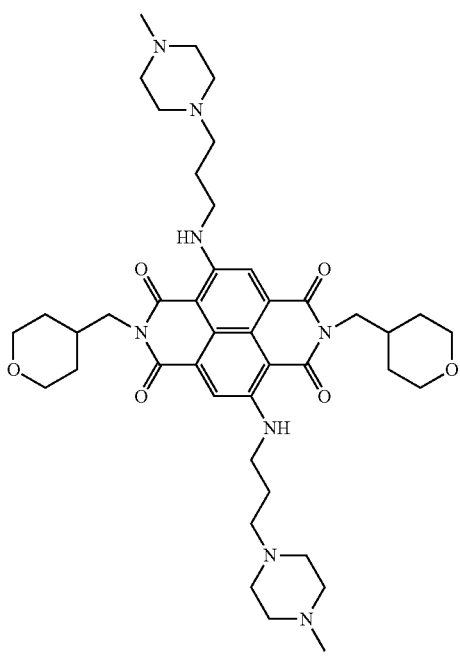

SKM38

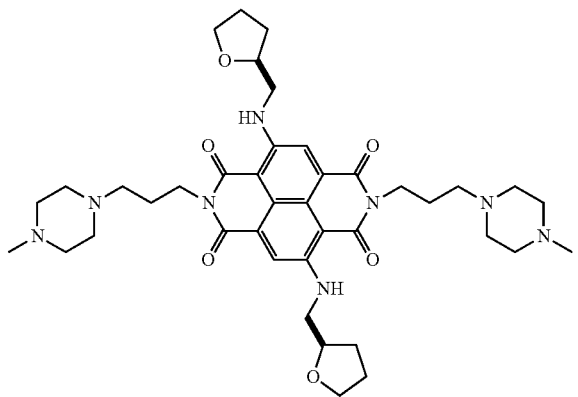

SKM22

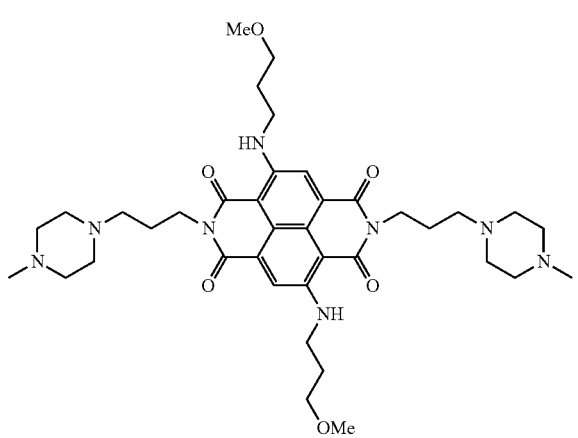

MM43

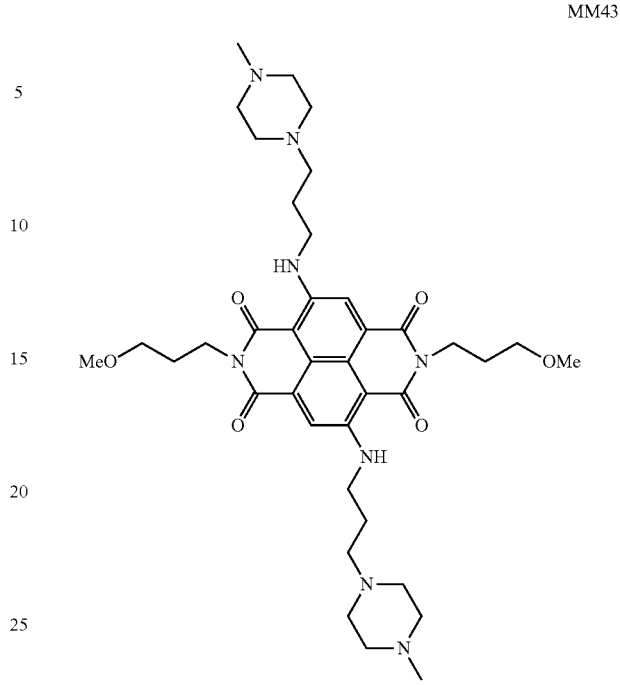

MATERIALS AND METHODS

Figure 1:
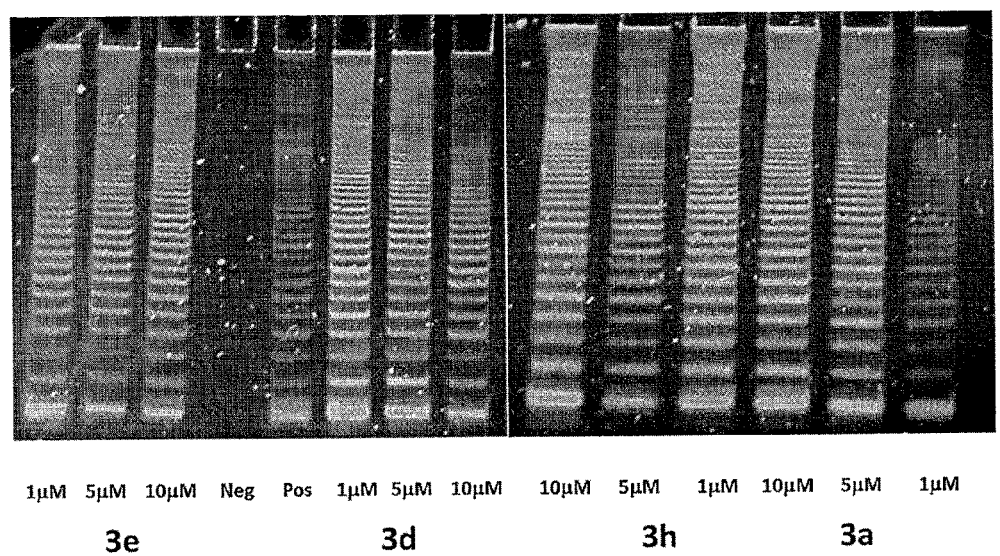
FIG. 1. Gel showing telomerase activity in MIA-Pa-Ca-2 cells treated with compound 3h after seven days of treatment. Lane 1; untreated cells, lanes 2-4; cells treated increasing concentrations of 3h. Telomerase activity was assessed using the TRAP-LIG assay as described in Materials and Methods. Compound concentrations are indicated. Neg; untreated cells, Pos; positive control. Neg: negative control with telomerase but no ligand.

Chemistry.

All chemicals, reagents and solvents were purchased from Sigma-Aldrich, Alfa Aesar, Lancaster Synthesis and Fluorochem (UK) and used without further purification. Solvents were supplied by VWR and Fisher scientific. Column chromatography was performed using BDH silica gel (BDH 153325P). HPLC analysis was carried out with a Gilson apparatus combining a 322 PUMP and an Agilent 1100 SERIES detector, using a C18 5μ (100×4.6 mm) column (41622271 (W), YMC, Japan), at a flow of 1 mL/min. Preparative HPLC was carried out with a Gilson apparatus combining a 322 PUMP and a UV/VIS-155 detector with detection at 280 nm, using a C18 5μ (100×20 mm) column (201022272) (W), YMC, Japan, at a flow of 20 mL/min. Water and methanol with 0.1% formic acid were used as solvents for HPLC. For the purification of compounds 3d, 3f-h, the following method was used: 100% aqueous solution for 5 min after injection, then gradually decreased to 60% aqueous solution over 25 min. For compounds 3a-c and 3e, the following method was used: 100% aqueous solution for 2 min after injection, gradually decreased to 20% aqueous solution over 17 minutes. For the HPLC purity analysis of compounds 3a-h, the method used was: 100% aqueous solution for 5 min after injection, to 60% w/v aqueous solution over 18 min as well as 100% aqueous for 5 min after injection, to 60% w/v aqueous over 43 min. Purity for final compounds was greater than 95% (HPLC, 280 nm). NMR spectra were recorded at 400 MHz ($^1$H NMR) or 500 MHz ($^{13}$C NMR) on a Bruker spectrometer in CDCl$_3$ (with 0.05% TMS, Cambridge Isotope Laboratories, USA). NMR spectra were analyzed with MestReC 4.5.6.0 with chemical shifts using TMS as a standard (δ=0 ppm). NMR multiplicity abbreviations are s (singlet), bs (broad singlet), d (doublet), t (triplet), q (quartet), 5q (quintet), and m (multiplet). Coupling constants J are reported as observed in Hertz (Hz). High Resolution Mass spectra (HRMS) were measured on a Micromass Q-TTOF Ultima Global tandem mass spectrometer run under electrospray ionisation (ESI), and processed using the MassLab 3.2 software. For compounds 2a-f no $^{13}$C NMRs were obtained due to solubility issues.

Compound 1 was prepared according to literature procedures.[4] Analytical data and $^1$H and $^{13}$C NMR spectra matched literature values.

Compounds 2a-f were prepared according to general procedure A.[5]

4,9-Dibromo-2,7-bis((tetrahydrofuran-2-yl)methyl) benzo[lmn][3,8]phenanthroline-1,3,6,8(2H,7H)-tetraone (2a)

2,6-dibromonaphthalene-1,4,5,8-tetracarboxylic dianhydride (1), (0.2 g, 0.47 mmol) and tetrahydrofurfurylamine (0.2 mL, 1.9 mmol) were suspended in acetic acid (14 ml) and refluxed for 5 h. After having been cooled to room temperature the precipitate was filtered and washed with water (50 mL) to give the title compound as an orange semi-solid (0.077 g, 28% yield). $^1$H NMR (400 MHz, CDCl$_3$, TMS): δ 8.76 (s, 2H), 4.51-4.39 (m, 4H), 4.13-4.09 (m, 2H), 3.99-3.93 (m, 2H), 3.79-3.73 (m, 2H), 2.15-2.03 (m, 4H), 1.99-1.88 (m, 2H), 1.80-1.71 (m, 2H).

4,9-dibromo-2,7-bis(furan-2-ylmethyl)benzo[lmn][3,8]phenanthroline-1,3,6,8(2H,7H)-tetraone (2b)

Compound 1 (0.3 g, 0.7 mmol), furfurylamine (0.2 mL, 2.1 mmol) and acetic acid (21 mL) were reacted according to general procedure A. Compound 2b was obtained as an orange semi-solid (0.160 g, 39% yield). $^1$H NMR (400 MHz, DMSO, TMS): δ 8.80-8.73 (m, 2H), 7.58-7.57 (m, 2H), 6.46-6.40 (m, 4H), 5.28-5.26 (m, 4H).

4,9-dibromo-2,7-bis((tetrahydro-2H-pyran-4-yl) methyl)benzo[lmn][3,8]phenanthroline-1,3,6,8(2H,7H)-tetraone (2c)

Compound 1 (0.3 g, 0.7 mmol), 4-(aminomethyl)-tetrahydropyran (0.2 g, 2.1 mmol) and acetic acid (21 mL) were reacted according to general procedure A.

Compound 2c was obtained as an orange semi-solid (0.1 g, 23% yield) and was used without further purification.

4,9-dibromo-2,7-bis(3-morpholinopropyl)benzo[lmn][3,8]phenanthroline-1,3,6,8-(2H,7H)-tetraone (2d)

Compound 1 (0.3 g, 0.7 mmol), 3-morpholinopropylamine (0.3 mL, 2.1 mmol), and acetic acid (21 mL) were reacted according to general procedure A. Compound 2d was obtained as an orange semi-solid (0.15 g, 32% yield). $^1$H NMR (400 MHz, CDCl$_3$, TMS): δ 8.99-8.76 (m, 2H), 4.33-4.28 (m, 4H), 3.54-3.52 (m, 8H), 2.53-2.50 (m, 4H), 2.45-2.37 (m, 8H), 2.00-1.92 (m, 4H).

4,9-dibromo-2,7-bis(3-methoxypropyl)benzo[lmn][3,8]phenanthroline-1,3,6,8(2H,7H)-tetraone (2e)

Compound 1 (0.3 g, 0.7 mmol), 3-methoxypropylamine (0.2 mL, 2.1 mmol) and acetic acid (21 mL) were reacted according to general procedure A. Compound 2e was obtained as an orange semi-solid (0.1 g, 25% yield). $^1$H NMR (400 MHz, CDCl$_3$, TMS): δ 8.99 (s, 2H), 4.36-4.30 (m, 4H), 3.55-3.51 (m, 4H), 3.31-3.28 (m, 6H), 2.06-2.00 (m, 4H).

4,9-dibromo-2,7-bis(2-morpholinoethyl)benzo[lmn] [3,8]phenanthroline-1,3,6,8(2H,7H)-tetraone (2f)

Compound 1 (1 g, 2.3 mmol), 4-(2-aminoethyl)morpholine (0.9 mL, 7 mmol) and acetic acid (60 mL) were treated according to general procedure A. Compound 2f was obtained as an orange semi-solid (0.2 g, 14% yield). $^1$H NMR (400 MHz, CDCl$_3$, TMS): δ 8.99 (s, 1H), 8.76 (s, 1H), 4.37 (t, 4H, J=6.4 Hz), 3.66-3.64 (m, 8H), 2.74-2.70 (m, 4H), 2.58-2.53 (m, 8H).

General procedure B. Compounds 3a-h were prepared according to general procedure B.

4,9-bis((3-(4-methylpiperazin-1-yl)propyl)amino)-2, 7-bis((tetrahydrofuran-2-yl)methyl)benzo[lmn][3,8] phenanthroline-1,3,6,8(2H,7H)-tetraone (3a)

Compound 2a (0.04 g, 0.067 mmol), 1-(3-aminopropyl)-4-methylpiperazine (0.06 mL, 0.3 mmol) and NMP (0.5 mL) were suspended in a microwave reaction vessel. The tube was flushed with argon, sealed and heated overnight (120° C.). After having been cooled to room temperature, the solvent was concentrated in vacuo and the crude mixture was purified by preparative HPLC. Compound 3a was obtained as a blue semi-solid (0.02 g, 40% yield). $^1$H NMR (400 MHz, CDCl$_3$, TMS): δ 9.49-9.43 (m, 2H), 8.18 (s, 2H), 4.46-4.41 (m, 2H), 4.37-4.33 (m, 2H), 4.16-4.07 (m, 2H), 3.98-3.93 (m, 2H), 3.77-3.71 (m, 2H), 3.59-3.57 (m, 4H), 2.96-2.82 (m, 8H), 2.78-2.65 (m, 8H), 2.60-2.56 (m, 10H), 2.11-2.00 (m, 4H), 1.98-1.88 (m, 8H). $^{13}$C NMR (100 MHz, CDCl$_3$, TMS): δ 166.2, 163.3, 149.2, 125.8, 121.3, 118.6, 101.9, 76.4, 67.9, 55.4, 54.3, 51.7, 44.8, 43.7, 41.4, 29.6, 26.4, 25.3. HRMS (ES$^+$) calculated for (M+H)$^+$ C$_{40}$H$_{56}$N$_8$O$_6$ 746.4480. found 746.4450.

2,7-bis(furan-2-ylmethyl)-4,9-bis((3-(4-methylpiperazin-1-yl)propyl)amino)benzo[lmn][3,8]phenanthroline-1,3,6,8(2H,7H)-tetraone (3b)

Compound 2b (0.15 g, 0.26 mmol), 1-(3-aminopropyl)-4-methylpiperazine (0.13 mL, 0.77 mmol) and NMP (1 mL) were reacted according to general procedure B. Compound 3b was obtained as a blue semi-solid (0.03 g, 16% yield). $^1$H NMR (400 MHz, CDCl$_3$, TMS): δ 9.45 (t, 2H, J=5.4 Hz), 8.19 (s, 2H), 7.32-7.31 (m, 2H), 6.39-6.38 (m, 2H), 6.32-6.31 (m, 2H), 5.36 (s, 4H), 3.59 (q, 4H, J=6 Hz), 3.04 (bs, 8H), 2.73 (bs, 8H), 2.59-2.56 (m, 10H), 1.93 (5q, 4H, J=6.4 Hz, 6 Hz). $^{13}$C NMR (100 MHz, CDCl$_3$, TMS): δ 165.5, 162.7, 150.2, 149.2, 142.0, 125.7, 121.2, 118.7, 110.6, 109.0, 101.8, 55.2, 53.3, 50.9, 43.8, 41.4, 36.3, 26.2. HRMS (ES$^+$) calculated for (M+H)$^+$ C$_{40}$H$_{48}$N$_8$O$_6$ 737.3775. found 737.3742.

4,9-bis((3-(4-methylpiperazin-1-yl)propyl)amino)-2, 7-bis((tetrahydro-2H-pyran-4-yl)methyl)benzo[lmn] [3,8]phenanthroline-1,3,6,8(2H,7H)-tetraone (3c)

Compound 2c (0.1 g, 0.16 mmol), 1-(3-aminopropyl)-4-methylpiperazine (0.1 mL, 0.48 mmol) and NMP (1 mL) were reacted according to general procedure B. Compound 3c was obtained as a blue semi-solid (0.025 g, 20% yield). $^1$H NMR (400 MHz, CDCl$_3$, TMS): δ 9.41 (t, 2H, J=5.4 Hz), 8.18 (s, 2H), 4.14 (d, 4H, J=7.2 Hz), 3.99-3.96 (m, 4H), 3.59 (q, 4H, J=6.4 Hz, 6 Hz), 3.38-3.32 (m, 4H), 2.54-2.50 (m, 16H), 2.30 (s, 6H), 2.20-2.10 (m, 2H), 1.97 (5q, 4H, J=6.8 Hz, 7.2 Hz), 1.66-1.48 (m, 12H). $^{13}$C NMR (100 MHz, CDCl$_3$, TMS): δ 166.4, 163.4, 149.3, 125.7, 121.2, 118.6, 101.8, 67.7, 55.8, 55.1, 53.3, 46.1, 45.4, 41.4, 34.4, 30.9, 26.7. HRMS (ES$^+$) calculated for (M+H)$^+$ C$_{42}$H$_{60}$N$_8$O$_6$ 774.4792. found 774.4806.

4,9-bis((3-(4-methylpiperazin-1-yl)propyl)amino)-2, 7-bis(3-morpholinopropyl)benzo[lmn][3,8]phenanthroline-1,3,6,8(2H,7H)-tetraone (3d)

Compound 2d (0.1 g, 0.15 mmol), 1-(3-aminopropyl)-4-methylpiperazine (0.06 mL, 0.37 mmol) and NMP (1 mL) were reacted according to general procedure B. Compound 3d was obtained as a blue semi-solid (0.015 g, 12% yield). $^1$H NMR (400 MHz, CDCl$_3$, TMS): δ 9.38 (t, 2H, J=5.4 Hz), 8.12 (s, 2H), 4.24 (t, 4H, J=6.8 Hz), 3.61 (t, 8H, J=4.4 Hz), 3.57 (q, 4H, J=6.8 Hz, 6.4 Hz), 2.53-2.44 (m, 30H), 2.30 (s, 6H), 1.99-1.88 (m, 8H). $^{13}$C NMR (100 MHz, CDCl$_3$, TMS): δ 166.1, 163.1, 149.1, 125.7, 121.1, 118.3, 101.9, 67.0, 56.5, 55.8, 55.0, 53.6, 53.2, 46.0, 41.3, 38.8, 26.7, 24.7. HRMS (ES$^+$) calculated for (M+H)$^+$ C$_{44}$H$_{66}$N$_{10}$O$_6$ 831.5245. found 831.5242.

2,7-bis(3-methoxypropyl)-4,9-bis((3-(4-methylpiperazin-1-yl)propyl)amino)benzo[lmn][3,8]phenanthroline-1,3,6,8(2H,7H)-tetraone (3e)

Compound 2e (0.051 g, 0.09 mmol), 1-(3-aminopropyl)-4-methylpiperazine (0.04 mL, 0.2 mmol) and NMP (0.5 mL) were treated according to general procedure B. Compound 3e was obtained as a blue semi-solid (0.018 g, 27% yield). $^1$H NMR (500 MHz, CDCl$_3$, TMS): δ 9.37 (t, 2H, J=5.4 Hz), 8.06 (s, 2H), 4.24 (t, 4H, J=7 Hz), 3.55-3.49 (m, 8H), 3.33 (s, 6H), 2.77-2.51 (m, 20H), 2.34 (s, 6H), 2.00-1.92 (m, 8H). $^{13}$C NMR (125 MHz, CDCl$_3$, TMS): δ 165.9, 162.9, 149.0, 125.5, 121.0, 118.2, 101.7, 70.6, 58.6, 55.7, 54.6, 52.7, 45.5, 41.4, 37.9, 28.2, 26.6. HRMS (ES$^+$) calculated for (M+H)$^+$ C$_{38}$H$_{56}$N$_8$O$_6$ 721.4401. found 721.4437.

4,9-bis((3-(4-methylpiperazin-1-yl)propyl)amino)-2, 7-bis(2-morpholinoethyl)benzo[lmn][3,8]phenanthroline-1,3,6,8(2H,7H)-tetraone (3f)

Compound 2f (0.1 g, 0.15 mmol), 1-(3-aminopropyl)-4-methylpiperazine (0.06 mL, 0.3 mmol) and NMP (0.5 mL) were reacted according to general procedure B. Compound 3f was obtained as a blue semi-solid (0.018 g, 15% yield). $^1$H NMR (400 MHz, CDCl$_3$, TMS): δ 9.36 (t, 2H, J=5.4 Hz), 8.14 (s, 2H), 4.45 (t, 4H, J=6.8 Hz), 3.84-3.82 (m, 8H), 3.64 (q, 4H, J=6.4 Hz, 5.6 Hz), 3.24 (bs, 8H), 3.03-2.84 (m, 20H), 2.75 (s, 6H), 2.73-2.69 (m, 4H), 2.00 (5q, 4H, J=6.8 Hz, 6.4 Hz). $^{13}$C NMR (100 MHz, CDCl$_3$, TMS): δ 166.0, 163.1, 149.2, 125.7, 121.2, 118.4, 101.9, 65.4, 55.4, 54.6, 52.9 (x2C), 50.0, 43.3, 40.9, 35.7, 25.9. HRMS (ES$^+$) calculated for (M+H)$^+$ C$_{42}$H$_{62}$N$_{10}$O$_6$ 803.4932. found 803.4963.

4,9-bis((2-(4-methylpiperazin-1-yl)ethyl)amino)-2,7-bis(2-morpholinoethyl)benzo[lmn][3,8]phenanthroline-1,3,6,8(2H,7H)-tetraone (3g)

Compound 2f (0.1 g, 0.15 mmol), 1-(2-aminoethyl)-4-methylpiperazine (0.05 mL, 0.37 mmol) and NMP (0.5 mL) were reacted according to general procedure B. Compound 3g was obtained as a blue semi-solid (0.020 g, 17% yield). $^1$H NMR (400 MHz, CDCl$_3$, TMS): δ 9.59-9.56 (m, 2H), 8.19 (s, 2H), 4.41 (t, 4H, J=6.4 Hz), 3.77-3.62 (m, 12H), 3.13 (bs, 8H), 2.91-2.66 (m, 30H). $^{13}$C NMR (100 MHz, CDCl$_3$, TMS): δ 165.9, 163.0, 148.9, 125.8, 121.4, 118.7, 102.3, 66.6, 55.9, 55.9, 53.7, 53.6, 50.2, 43.7, 40.2, 36.8. HRMS (ES$^+$) calculated for (M+H)$^+$ C$_{40}$H$_{58}$N$_{10}$O$_6$ 776.4698. found 776.4660.

4,9-bis((2-(4-methylpiperazin-1-yl)ethyl)amino)-2,7-bis(3-morpholinopropyl)benzo[lmn][3,8]phenanthroline-1,3,6,8(2H,7H)-tetraone (3h)

Compound 2d (0.3 g, 0.44 mmol), 1-(2-aminoethyl)-4-methylpiperazine (0.16 mL, 1.1 mmol) and NMP (0.7 mL) were reacted according to general procedure B. Compound 3h was obtained as a blue semi-solid (0.025 g, 7% yield). $^1$H NMR (500 MHz, CDCl$_3$, TMS): δ 9.49-9.47 (m, 2H), 8.09 (s, 2H), 4.17-4.20 (m, 10H), 3.66 (t, 6H, J=4 Hz), 3.55 (q, 4H, J=5.5 Hz, 5.5 Hz), 3.02 (bs, 6H), 2.81-2.78 (m, 10H), 2.62-2.59 (m, 16H), 1.98-1.92 (m, 4H). $^{13}$C NMR (125 MHz, CDCl$_3$, TMS): δ 166.0, 163.1, 148.9, 125.8, 121.3, 118.7, 102.3, 66.1, 56.0, 55.9, 53.6, 53.0, 50.3, 43.6, 40.1, 38.44, 24.1. HRMS (ES$^+$) calculated for (M+H)$^+$ C$_{42}$H$_{62}$N$_{10}$O$_6$ 803.4932. found 803.4952.

FRET Assay.

The ability of the naphthalene diimide compounds to stabilize DNA sequences was investigated using a fluorescence resonance energy transfer (FRET) assay modified to be used as a high-throughput screen in a 96-well format. Several quadruplex sequences were studied (the human telomeric G-quadruplex DNA sequence 5'-FAM-d(GGG[TTAGGG]$_3$)-TAMRA-3' and the duplex sequence 5'-FAM-dTATAGCTATA-HEG-TATAGCTATA-TAMRA-3' (HEG linker: [(—CH$_2$—CH$_2$—O—)$_6$])), as well as two overlapping sequences from the HSP90 promoter region (HSP90a and HSP90b):

HSP90a: 5'-FAM-d(GGGCCAAAGGGAAGGGGTGGG)-TAMRA-3'

HSP90b: 5'-FAM-d(GGGCGGGCCAAAGGGAAGGGG)-TAMRA-3'

The labelled oligonucleotides have attached to them the donor fluorophore FAM: 6-carboxyfluorescein and the acceptor fluorophore TAMRA: 6-carboxytetramethylrhodamine. The FRET probe sequences were diluted from stock to the correct concentration (400 nM) in a 60 mM potassium cacodylate buffer (pH 7.4) and then annealed by heating to 85° C. for 10 min, followed by cooling to room temperature in the heating block. The compound was stored as a 10 mM stock solution in DMSO; final solutions (at 2×concentration) were prepared using 10 mM HCl in the initial 1:10 dilution, after which 60 mM potassium cacodylate buffer (pH 7.4) was used in all subsequent steps. The maximum HCl concentration in the reaction volume (at a ligand concentration of 20 µM) is thus 200 µM, well within the range of the buffer used. Relevant controls were also performed to check for interference with the assay. 96-Well plates (MJ Research, Waltham, Mass.) were prepared by aliquoting 50 µl of the annealed DNA into each well, followed by 50 µl of the compound solutions. Measurements were made on a DNA Engine Opticon (MJ Research) with excitation at 450-495 nm and detection at 515-545 nm. Fluorescence readings were taken at intervals of 0.5° C. in the range 30-100° C., with a constant temperature being maintained for 30 s prior to each reading to ensure a stable value. Final analysis of the data was carried out using a script written in the program Origin 7.0 (OriginLab Corp., Northampton, Mass.). The advanced curve-fitting function in Origin 7.0 was used for calculation of $\Delta T_m$ values. All determinations were performed in triplicate or better. Esds in $\Delta T_m$ are ±0.1° C.

Cell Culture and Cytotoxicity Testing.

Human cancer cell lines, MCF7 (breast), A549 (lung), Mia-PaCa2, PANC1 and HPAC (pancreatic), RCC4 and 786-0 renal, and the somatic human cell line WI-38 (lung fibroblast) were purchased from ATCC. Cell lines were maintained in appropriate medium supplemented with 10% foetal bovine serum (Invitrogen, UK), 2 mM L-glutamine (Invitrogen, Netherlands), and other components as specified by the suppliers. Cell lines were maintained at 37° C., 5% CO$_2$ and routinely passaged. Drugs were dissolved in DMSO and filtered through 0.22 µm pore-size filter units before addition to cell line appropriate media. Cellular growth inhibition was measured using the sulforhodamine B (SRB) assay in 96 well plates as described previously.[1,2] Fifty percent inhibitory concentrations (IC$_{50}$) were determined by taking the mean absorbance at 540 nm for each drug concentration expressed as a percentage of the absorbance of untreated control wells.

For qRT-PCR analysis, Mia-PaCa2 cells were seeded to a density equivalent to that used for IC$_{50}$ determinations in T75 culture flasks and grown for 24 h in 10 ml DMEM to allow attachment before addition of compound 3d to the culture medium. Following compound exposure, cells were washed twice in PBS, harvested by trypsinisation, collected by centrifugation (300 g, 5 min, 4° C.) and re-suspended in RLT buffer (Qiagen). Samples were homogenised using QIAshredder spin columns and stored at −80° C. prior to RNA extraction. Three biological replicates were performed on separate days.

Determination of Cellular Telomerase Activity.

Telomerase activity was determined using the TRAP-LIG assay, a modified telomere repeat amplification protocol that ensures that there is no carry-over of ligand into the second PCR step of the assay. Briefly, 1 µg of protein from untreated and treated cells were incubated with TS forward primer (0.1 µg of 5'-AAT CCG TCG AGC AGA GTT-3') at 30° C. for 10 min to allow the initial elongation to take place. Elongated products were purified using the QIAquick nucleotide purification kit (Qiagen) according to the manufacturer's instructions. Eluted samples were freeze-dried and re-dissolved in PCR grade water. Re-dissolved PCR products were subjected to amplification in master mix containing ACX reverse primer (1 µM, 5'-GCG CGG [CTTACC]$_3$ CTA ACC-3'), TS forward primer (0.1 µg), TRAP buffer, BSA (5 µg), 0.5 mM dNTPs, and 2U RedHot TAQ polymerase (ABgene, U.K.) for 35 cycles of 94° C. for 30 s, 61° C. for 1 min, and at 72° C. for 1 min. Samples were separated by PAGE and visualized with SYBR green (Aldrich).

Transcriptional Analysis.

The expression of (i) 83 key human genes involved in telomere replication and maintenance, and (ii) 83 human genes involved in DNA damage signaling responses, was assessed using PCR arrays (SABiosciences). Total RNA was extracted from approximately 1×10$^7$ Mia-PaCa2 cells treated for 24 h with compound 3d, using the RNeasy kit (Qiagen) with on-column DNaseI treatment to remove residual genomic DNA. The quality of the harvested RNA was confirmed by nanodrop spectroscopy and by analysis with a Human RT$^2$ RNA QC PCR Array. First-strand cDNA synthesis was performed with the RT$^2$ first strand kit and qPCR was carried out using the RT$^2$ qPCR master mix (Qiagen) using 0.5 µg total RNA per array plate in a Stratagene MX-3000P instrument (Agilent, USA). Relative gene expression was determined by the ΔΔCT method using the web-based RT² Profiler™ PCR Array Data Analysis software (SABiosciences). Data were normalized to the geometric mean of five housekeeping genes (RPLP10, β-actin, B2M, GAPDH and HPRT1).

Senescence Staining.

Senescence detection and quantification experiments were carried out using the Senescence β-galactosidase staining kit (Cell Signalling Technology, MA, USA) according to the manufacturer's protocol. Briefly, $1\times10^5$ cells were seeded in 6-well plates in 2 ml of medium supplemented with the test compound and incubated for 24 h. Cells were washed (2 ml PBS), fixed (2% formaldehyde and 2% glutaraldehyde in PBS, 15 min, room temperature) and washed (2×2 ml PBS) before staining overnight. Senescent cells, detected by their blue pigmentation, were counted using a light microscope.

Biophysical Studies.

The ability of compounds 3a-h to stabilize a human telomeric quadruplex was assessed by a high-throughput FRET (Fluorescence Resonance Energy Transfer) melting technique. Table 1 also shows melting data obtained with a duplex DNA sequence. Table 1 shows that only the compounds containing morpholine rings showed significant telomeric quadruplex stabilization, as well as some binding to the duplex DNA sequence. The dimethoxy compound 3e has a very slight effect on the telomeric quadruplex used here but a large stabilizing effect on HSP90 promoter sequence quadruplexes (which are reported elsewhere to form stable quadruplexes), with $\Delta T_m$ values of 23.8° C. and 29.0° C. None of the furan tetrahydrofuran, pyranose or acyclic ether compounds has any effect on quadruplex or duplex stability. All of the morpholine derivatives produce high $T_m$ changes in the telomeric quadruplex, comparable to that previously noted for compound 4. However compounds 3f and 3g with an n=2 —$(CH_2)_n$— linker to the morpholine ring show superior selectivity for quadruplex over duplex DNA compared to the n=3 compounds.

TABLE 1

$\Delta T_m$ values (° C.) for a duplex DNA (T-loop), a human telomeric quadruplex sequence (htel) and two HSP90 quadruplex sequences, at a 1 μM ligand concentration (with 60 mM K⁺ at pH 7.4). Esds are ± 0.1° C., estimated from multiple readings. Data for compound 4 has been taken from reference 2. Data for the two preferred di-morpholine compounds has been highlighted.

| Compound | T-loop | Htel | HSP90A | HSP90B |
|---|---|---|---|---|
| 3a | 0.2 | 22.7 | 27.1 | 21.0 |
| 3b | 0.3 | 0.2 | 0.9 | 1.1 |
| 3c | 0.2 | 0.1 | 0.7 | 0.8 |
| 3d | 4.9 | 26.6 | 33.1 | 28.6 |
| 3e | 0.0 | 0.5 | 29.0 | 23.8 |
| 3f | 0.8 | 27.0 | 33.9 | 29.1 |
| 3g | 1.7 | 24.7 | 30.6 | 27.6 |
| 3h | 8.1 | 27.8 | 31.9 | 31.1 |
| 4 | 1.3 | 28.3 | 36.3 | 32.0 |

Biological Studies

The anti-proliferative activity of the group of nine ND derivatives was assessed using the SRB assay following 96 h exposure to 2-fold serial dilutions of each compound (Table 2) in a panel of cancer cell lines together with a normal fibroblast line. Compound 3a is devoid of significant anti-proliferative activity in all except the Mia-PaCa2 and A549 lines though all other compounds in this group (3b, 3c, 3e) had $IC_{50}$ values in the range of 1-8 μM, with compound 3c in particular showing up to 10-fold selectivity for the renal carcinoma cell line 786-0. In contrast the morpholine compounds all show sub-μM anti-proliferative activity in at least some of the cancer cell lines used and the two compounds 3d, 3h with n=3 —$(CH_2)_n$— linkers to the morpholine groups, show particularly potent activity in the Mia-PaCa2 and PANC1 pancreatic carcinoma and A549 lung adenocarcinoma cell lines ($IC_{50}$ values of 10-20 nM).

TABLE 2

Growth inhibition data for compounds 3a-h and 4 using a panel of cancer cell lines and a normal human fibroblast line (WI-38), measured by the SRB assay for 96 hr exposure and expressed as $IC_{50}$ values in μM. Comparable data for compound 4 has been previously reported.[2,3] The panel of cancer carcinoma cell lines used includes: A549 (lung), RCC4 and 786-0 (renal), MIA-PaCa2 (pancreatic), and MCF-7 (breast). Data for two preferred di-morpholine compounds has been highlighted.

|  | 3a | 3b | 3c | 3d | 3e | 3f | 3g | 3h | 4 |
|---|---|---|---|---|---|---|---|---|---|
| A549 | 5.57 ± 0.31 | 2.41 ± 0.01 | 2.92 ± 0.01 | <0.01 ± 0.005 | 2.54 ± 0.01 | 1.55 ± 0.02 | 4.93 ± 0.05 | <0.01 ± 0.006 | 0.11 ± 0.02 |
| RCC4 | >10 | 3.11 ± 0.06 | 8.38 ± 0.50 | 0.56 ± 0.05 | 10.51 ± 0.14 | 1.75 ± 0.18 | 5.10 ± 0.70 | 0.28 ± 0.06 | n/a |
| MIA-PaCa2 | 5.65 ± 0.14 | 2.83 ± 0.01 | 2.50 ± 0.01 | <0.01 ± 0.01 | 2.79 ± 0.09 | 0.04 ± 0.01 | n/a | 0.01 ± 0.01 | 0.11 ± 0.02 |
| 786-0 | >10 | 1.10 ± 0.03 | 1.20 ± 0.03 | 0.32 ± 0.01 | 7.17 ± 0.41 | 0.63 ± 0.06 | 1.48 ± 0.17 | n/a | n/a |
| MCF-7 | >10 | 2.61 ± 0.06 | 3.12 ± 0.13 | 0.07 ± 0.007 | 5.62 ± 0.15 | 0.17 ± 0.01 | 0.18 ± 0.03 | 0.03 ± 0.01 | 0.17 ± 0.03 |
| WI-38 | >10 | 6.84 ± 0.05 | 12.65 ± 0.11 | 0.23 ± 0.01 | 3.32 ± 0.50 | 0.61 ± 0.02 | 1.17 ± 0.11 | 2.46 ± 0.02 | 9.0 ± 3.2 |

Figure 2:
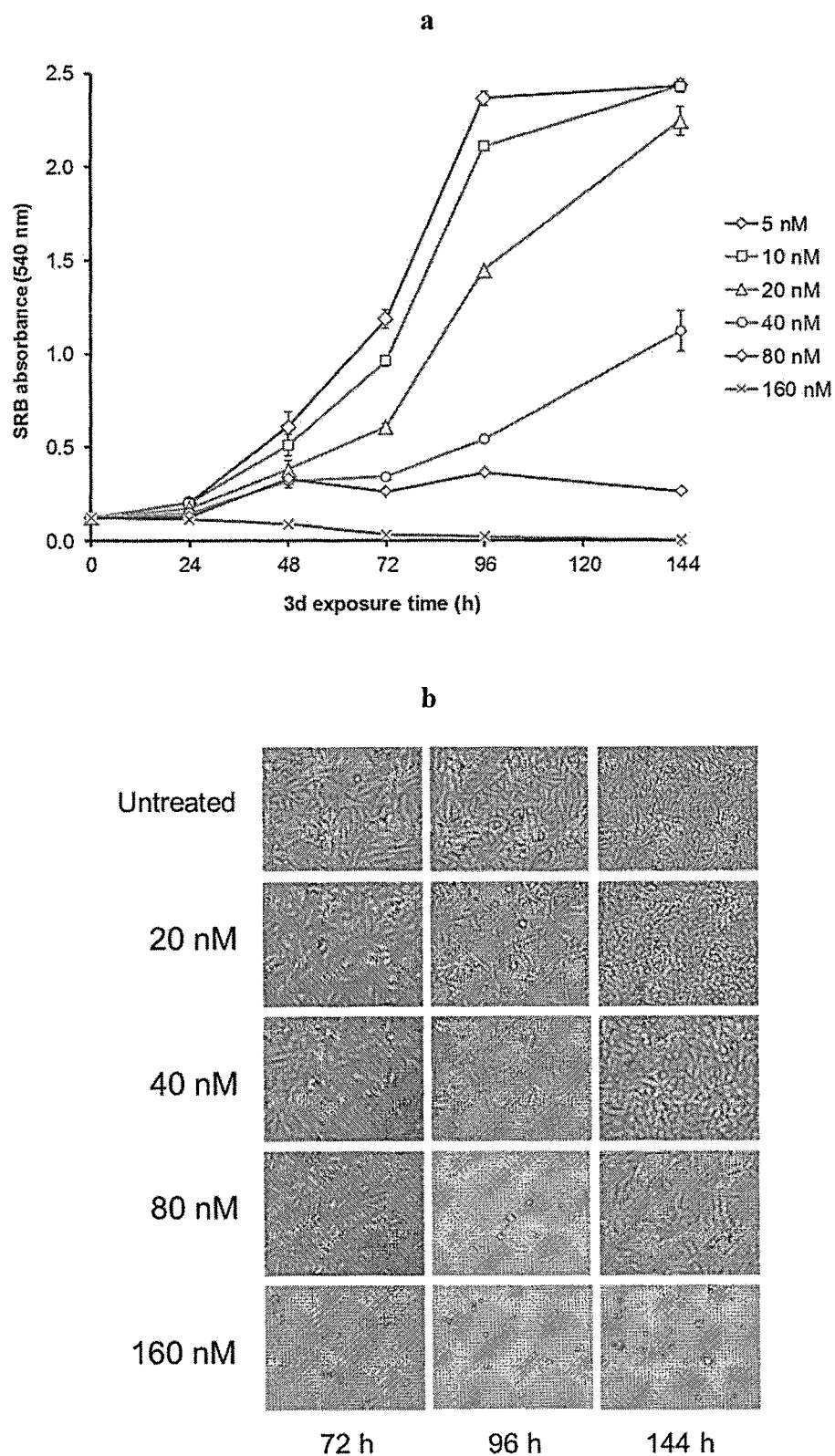
FIG. 2. Treatment of MiaPaCa2 cells with compound 3d elicits a limited and specific transcriptional response from genes controlling telomerase and telomere maintenance (a) Dose-response curves obtained prior to the array experiments. MiaPaCa2 cells were exposed to the indicated concentrations of compound 3d and growth measured every 24 h using the SRB assay as described in Materials and Methods. Data are the average of three independent replicates performed on separate days. Error bars represent standard deviation. (b) Representative micrographs of 3d-treated MiaPaCa2 cells. All images are at ×100 magnification. (c) Volcano plot summarising the qPCR data of transcriptional responses of genes involved in telomere maintenance pathways. Cells were exposed to 20 nM, 40 nM or 80 nM for 24 h and the transcriptional responses determined using qPCR arrays as described in Materials and Methods. P values were calculated from a Student's t-test of the replicate $2^{\Delta Ct}$ values for each gene in the control and treatment groups. Expression fold changes for each gene at each compound concentration are expressed relative to the solvent treated control. (d) Genes showing greater than 1.5-fold repression compared to solvent treated control. (e) Genes showing greater than 1.5-fold induction compared to solvent treated control. *, $P<0.05$, **, $P<0.01$.
Figure 2:
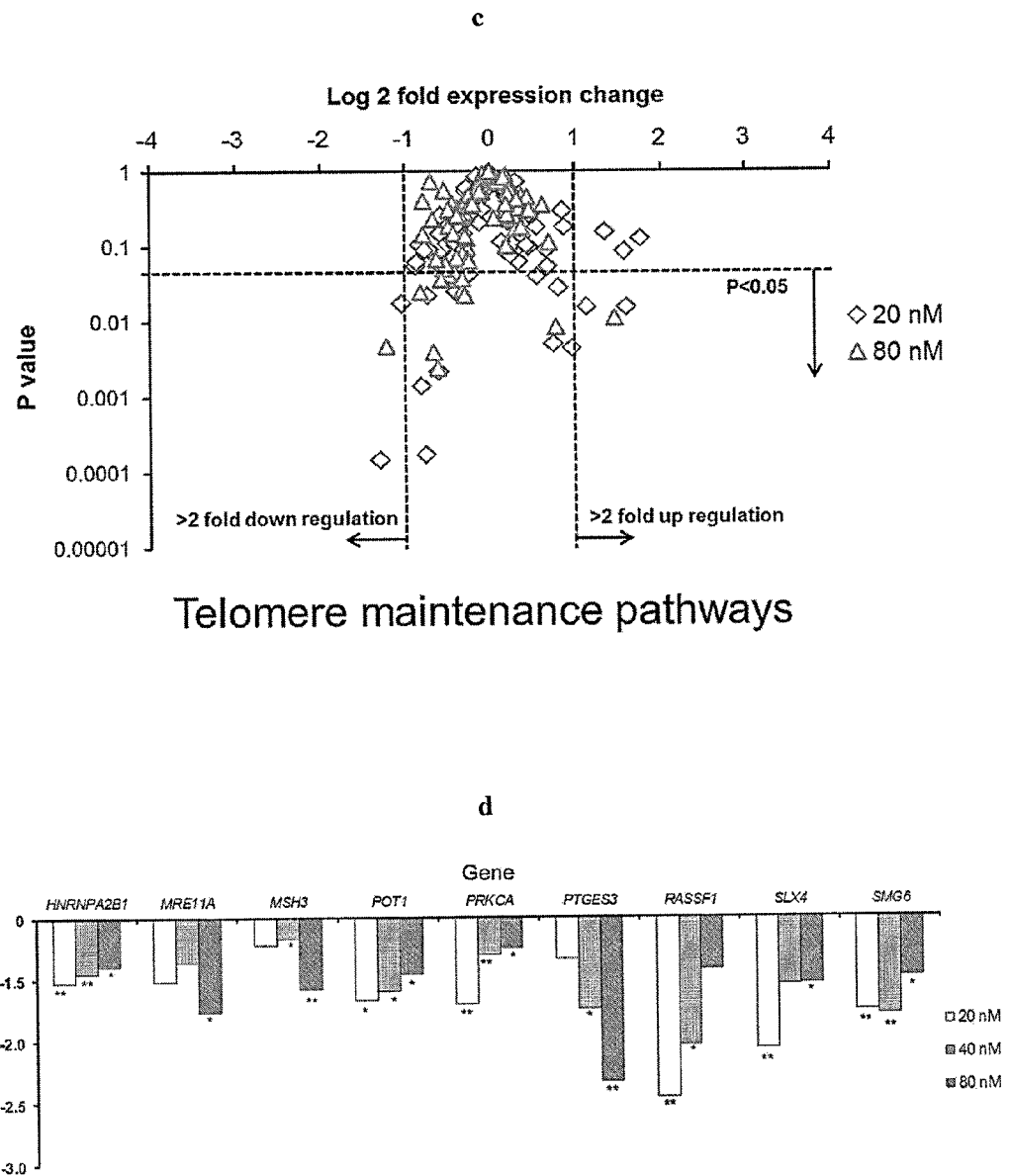
Figure 2:
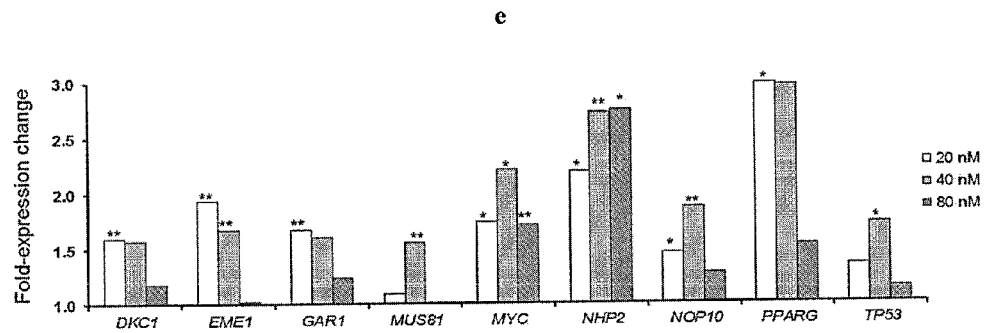

Dose-response curves were used to guide the choice of compound concentration and time-points for the array experiments (FIG. 2a). Exposure to between 5 nM and 40 nM of compound 3d resulted in titratable growth inhibition with subsequent full recovery of confluent growth at 144 h (FIG. 2b). Exposure to 80 nM of 3d resulted in no growth recovery, though cells remained viable, whereas at 160 nM no viable cells could be recovered by 72 h. To explore this response continuum the transcriptional signature of cells exposed for 24 h to 20 nM, 40 nM, 80 nM concentrations of 3d, or solvent alone as control, was analysed as described in Materials and Methods. It was expected that this time point would capture the early transcriptional signature responses to compound challenge that resulted in the differing levels of growth inhibition observed.

Analysis of 83 genes involved with telomere maintenance revealed modest responses to exposure to compound 3d (FIG. 2c). In total 30 genes were up or down-regulated compared to controls, to a statistically significant level (P<0.05, Student's t-test) by 20 nM, 40 nM or 80 nM of 3d compared with the solvent. However, changes in transcript abundance were modest, with only seven of these genes (MYC, NHP2, PPARG, PRKCB, PTEGES3, RASSF1 and SLX4) showing greater than two-fold abundance changes (FIGS. 2d and 2e). Overall this data set appeared consistent with the observed lack of telomerase inhibition for compound 3d, though it is notable that down-regulation of the gene encoding the telomere end-capping protein POT1 was observed, albeit on the borderline of statistical significance.

Figure 3:
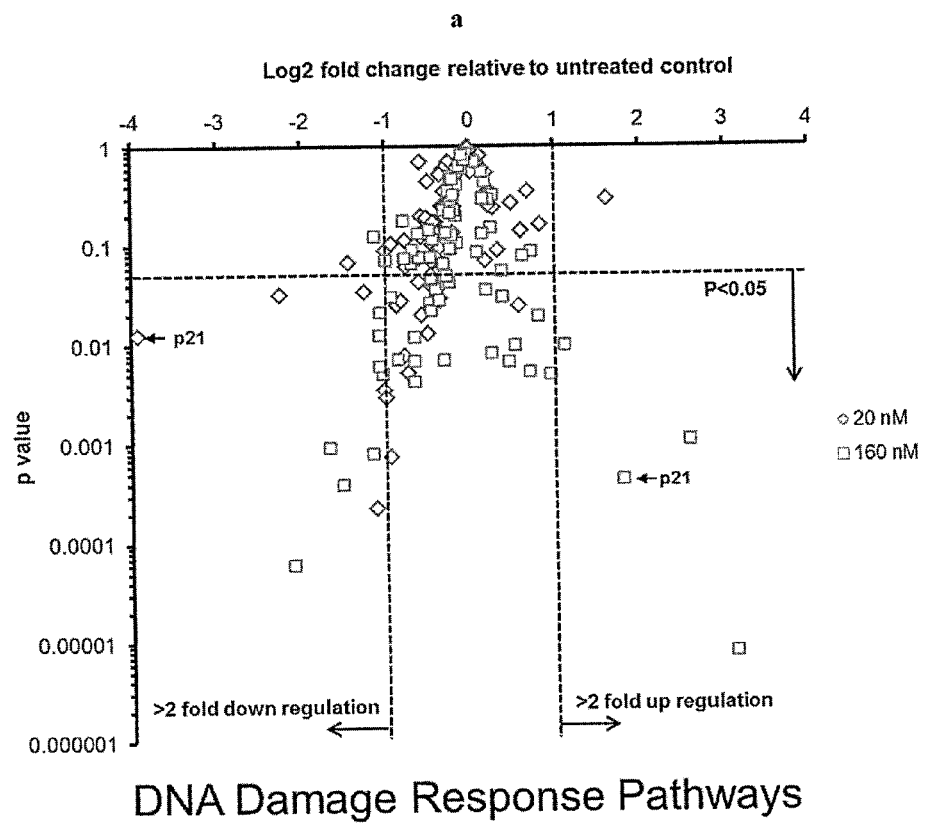
FIG. 3. Treatment of MiaPaCa2 cells with compound 3d produces a dynamic DNA damage response at the transcriptional level. (a) Volcano plot summarising the qPCR data of transcriptional responses of genes involved in DNA damage response pathways. Cells were exposed to 20 nM, 40 nM, 80 nM or 160 nM for 24 h and the transcriptional responses determined using qPCR arrays as described in Materials and Methods. P values were calculated from a Student's t-test of the replicate 2^ΔCt values for each gene in the control and treatment groups. Expression fold changes for each gene at each compound concentration are expressed relative to the solvent treated control. (b) Genes showing greater than 2-fold repression compared to solvent treated control. (c) and (d) Genes showing dynamic regulation following treatment with compound 3d. *, $P<0.05$, **, $P<0.01$.
Figure 3:
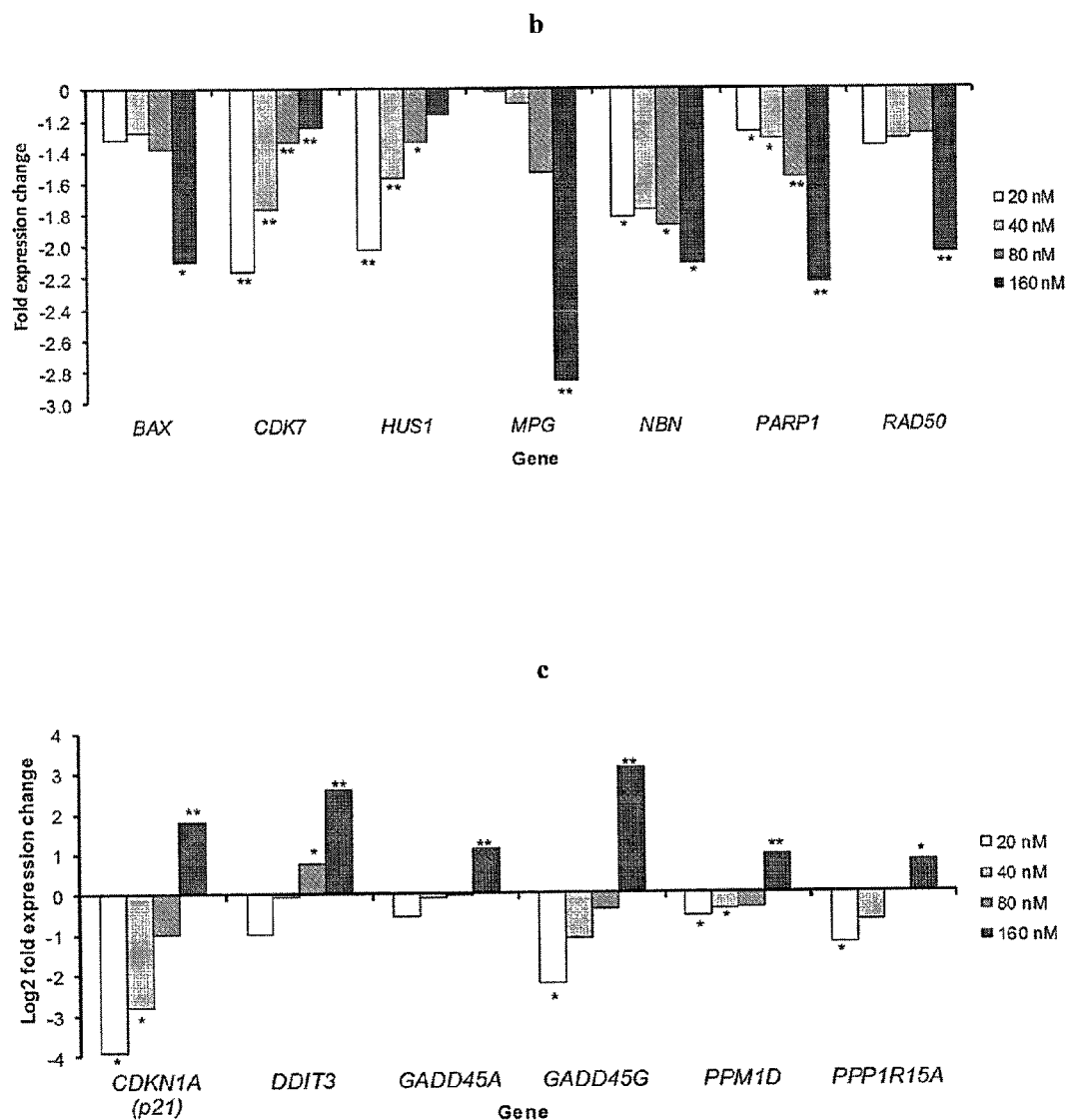
Figure 3:
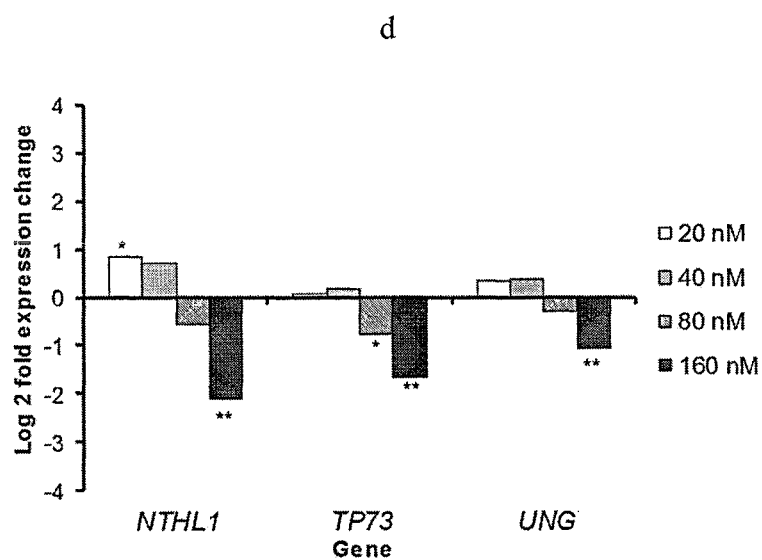

Various quadruplex-stabilising agents are known to induce pronounced DNA damage responses. We therefore next assessed the effect of 3d on the transcription of genes associated with DNA damage response and repair pathways. For these pathways the effect of a cytotoxic dosage of 3d (160 nM) on Mia-PaCa2 cells was also tested to assess the correlation between compound-induced DNA damage and cell killing. Of 83 genes tested, 16 were significantly increased or decreased greater than 2-fold in abundance following exposure to 20 nM, 40 nM, 80 nM or 160 nM of compound 3d (FIG. 3a). Three patterns of transcriptional response were identified within the DNA damage response gene set: i) seven genes that showed down-regulation only, notably BAX, PARP1, RAD50 and MPG (FIG. 3b); ii) six genes that were down-regulated at sub-cytotoxic concentrations but up-regulated at toxic concentrations, including CDKN1A, DDIT3 and GADD45G (FIG. 3c); iii) three genes that were up-regulated at sub-lethal concentrations and down-regulated at 160 nM (FIG. 8d). The latter two groups appeared to reflect a dynamic switch in the cellular response from low-level growth inhibition up to 40 nM of 3d to cytostatic then cytotoxic effects at 80 nM and 160 nM respectively.

Overall, the DNA damage response pathways were far more strongly affected than those pathways involving telomere maintenance, though there was no significant induction or repression of the major DNA damage checkpoint genes ATM and ATR. Furthermore there was no apparent induction of the γ-H2AX gene in Mia-PaCa2 cells following treatment with 3d (data not shown), indicating that any DNA damage induced by 3d does not involve double-stranded breaks. Instead the response was dominated by genes with roles in growth arrest and more general stress responses. Notably, CDKN1A, DDIT3 and GADD45G were all strongly down-regulated by the lower concentrations of 3d and strongly up-regulated at cytotoxic concentrations.

Figure 4:
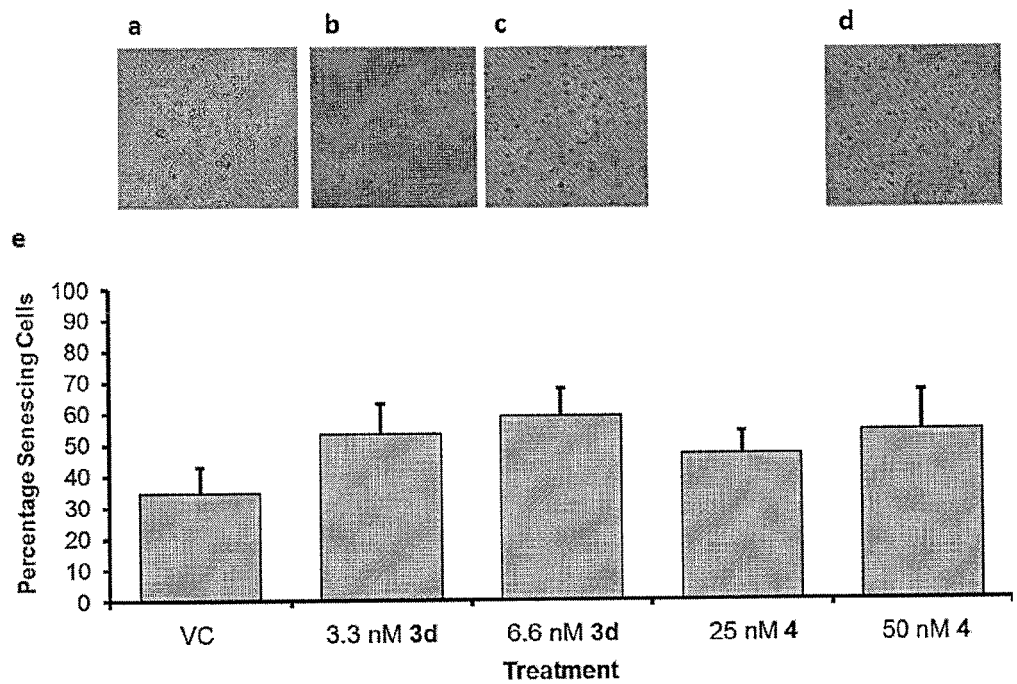
FIG. 4. Micrographs showing the results of staining for evidence of cellular senescence in MiaPaCa2 cells using the β-galactosidase assay. Senescent cells are coloured blue in this procedure. Staining was performed after seven days treatments with (a) vehicle control, ×100 magnification, (b) 3.3 nM of compound 3d, ×200 magnification, (c) 6.6 nM of compound 3d, ×200 magnification, (d) 50 nM of compound 4, ×200 magnification, (e) plot of the percentage of senescent cells at the indicated concentrations of compounds 3d and 4, compared to the background senescence in this cell line (with vehicle control only). Cell counts were performed in triplicate and error bars represent estimated standard deviations.

CDKN1A encodes the cyclin-dependent kinase p21WAF1 that induces replicative senescence, which is a well-studied consequence of telomerase inhibition and telomere maintenance disruption. We observed a strong induction of senescence in Mia-PaCa2 cells treated for 7 days with both compound 3d and 4 (FIG. 4). Compound 3d was ~10-fold more potent than 4 as an inducer of cellular senescence. Compounds 3b and 3d behaved in a similar manner to each other, with concentrations of 3-4 nM being sufficient to result in ~50-60% of cells becoming senescent after this time-course. Together these data suggest that both ND derivative sets cause growth arrest through induction of senescence, but that the route to this precedes through distinct telomerase-dependant (compound 4) and independent (compound 3d) pathways.

Structural Isomer Data

Next a series of structural isomers were tested. The data below shows the anti-proliferative activity, expressed as $IC_{50}$ values, obtained using the SRB assay with 96 hr exposure, for a panel of cancer and normal human fibroblast (WI38) cell lines.

|  | RCC4 | 786-O | MCF-7 | MiaPaCa2 | A549 | Panc1 | WI38 |
| --- | --- | --- | --- | --- | --- | --- | --- |
| SKM022 | 7.6 ± 0.01 | 16.1 ± 0.63 | 17.5 ± 0.98 | 7.05 ± 0.83 | 5.75 ± 0.51 | 2.5 ± 0.34 | >25 |
| MM43 | 10.51 ± 0.14 | 7.17 ± 0.41 | 5.62 ± 0.15 | 2.79 ± 0.09 | 2.54 ± 0.01 | n/a | 3.32 ± 0.5 |
| MM41 | 0.56 ± 0.05 | 0.32 ± 0.01 | 0.070 ± 0.007 | 0.01 ± 0.01 | 0.019 ± 0.005 | 0.003 ± 0.0005 | 0.23 ± 0.01 |
| SKM029 | 0.61 ± 0.07 | 0.44 ± 0.07 | 0.014 ± 0.001 | 0.05 ± 0.002 | 0.007 ± 0.001 | 0.002 ± 0.001 | 0.3 ± 0.023 |
| MM45 | 1.75 ± 0.18 | 0.63 ± 0.06 | 0.17 ± 0.01 | 0.04 ± 0.01 | 1.55 ± 0.02 | n/a | 0.61 ± 0.02 |
| SKM036 | 0.3 ± 0.016 | 0.16 ± 0.021 | 0.021 ± 0.001 | 0.005 ± 0.001 | 0.02 ± 0.001 | 0.005 ± 0.001 | 0.18 ± 0.002 |
| MM47 | 0.28 ± 0.06 | n/a | 0.03 ± 0.01 | 0.01 ± 0.01 | 0.023 ± 0.006 | n/a | 2.46 ± 0.02 |
| MM33 | 8.38 ± 0.50 | 1.2 ± 0.03 | 3.12 ± 0.13 | 2.5 ± 0.01 | 2.92 ± 0.01 | n/a | 12.65 ± 0.11 |
| SKM052 | 2.2 ± 0.015 | 0.29 ± 0.002 | 0.51 ± 0.017 | 0.137 ± 0.031 | 0.46 ± 0.01 | 1.1 ± 0.13 | 2.8 ± 0.23 |
| MM10 | >10 | >10 | >10 | 5.65 ± 0.93 | 5.57 ± 0.87 | n/a | >10 |
| SKM038 | 3.0 ± 0.17 | 0.39 ± 0.02 | 0.56 ± 0.034 | 0.095 ± 0.003 | 0.16 ± 0.002 | 1.5 ± 0.17 | 2.3 ± 0.08 |

The following data show the stabilisation of human telomeric (F21T) and HSP90 quadruplexes, expressed as changes in melting temperature. The T-loop sequence represents duplex DNA.

|  | F21T | | Hsp90A | | Hsp90B | | Tloop | |
| --- | --- | --- | --- | --- | --- | --- | --- | --- |
|  | 1 uM | 2 uM | 1 uM | 2 uM | 1 uM | 2 uM | 1 uM | 2 uM |
| SKM022 | <2 | 16 | 22 | 24 | 22 | 26 | 0 | 0 |
| MM43 | <2 | 22 | 29 | 32 | 24 | 29 | 0 | 0 |
| MM41 | 27 | 32 | 33 | 36 | 29 | 33 | 5 | 9 |
| SKM029 | 29 | 34 | 34 | 36 | 30 | 34 | 5 | 9 |
| MM45 | 27 | 31 | 34 | 36 | 29 | 34 | 0 | 1 |
| SKM036 | 26 | 31 | 33 | 36 | 28 | 32 | 2 | 8 |
| MM47 | 28 | 33 | 32 | 36 | 31 | 34 | 8 | 12 |
| MM33 | <2 | <2 | <2 | <2 | <2 | <2 | 0 | 0 |
| SKM052 | <2 | 22 | 2 | 27 | 3 | 23 | 0 | 0 |

-continued

|  | F21T | | Hsp90A | | Hsp90B | | Tloop | |
| --- | --- | --- | --- | --- | --- | --- | --- | --- |
|  | 1 uM | 2 uM | 1 uM | 2 uM | 1 uM | 2 uM | 1 uM | 2 uM |
| MM10 | 23 | 26 | 27 | 30 | 21 | 28 | 0 | 0 |
| SKM038 | <2 | 15 | 21 | 23 | 13 | 17 | 0 | 0 |

In Vivo Data

Balb/c female mice (7-8 weeks old) were housed in microisolator cages, fed with commercial mouse food (Food Harlam 2018, Madison, USA) and allowed to acclimatise for seven days before any procedure. Following a bolus IV injection of 3d at 20 mg/kg (IV 100 uL/10g body weight in sterile PBS) the Cmax was 1.6 uM and the half-life was 4 hours. There was no detectable drug at 24 hours.

CD1 nu/nu female mice (7-8 weeks old) were housed in microisolator cages, fed with commercial mouse food (Food Harlam 2018, Madison, USA) and allowed to acclimatise for seven days before any procedure. Exponentially growing MiaPaca-2 cells ($5\times10^6$ cell/100 uL unsupplemented RPMI) were inoculated subcutaneously into the right flank (100 uL per mice). Measurements of tumour growth were carried out at least twice a week with digital callipers until tumour masses reached an average size of 0.1 cm$^3$. Tumour volume was calculated by using the standard formula for determining the volume of an ellipsoid ($[length \times width \times depth \times \pi]/6$)).

In a first experiment, mice were allocated into groups (six mice per group) as follows: control group (IV 100 uL/10g sterile PBS) and single dose of 20 mg/kg of 3d (IV 100 uL/10 g body weight in sterile PBS). The observations finished when tumours reached a size of 1 cm$^3$ or when mice showed weight loss of up to 20%. Following a single dose of 3d at 20 mg/kg a significant growth delay in Mia-Paca2 human pancreatic tumour xenografts was observed compared to untreated controls.

Figure 5:
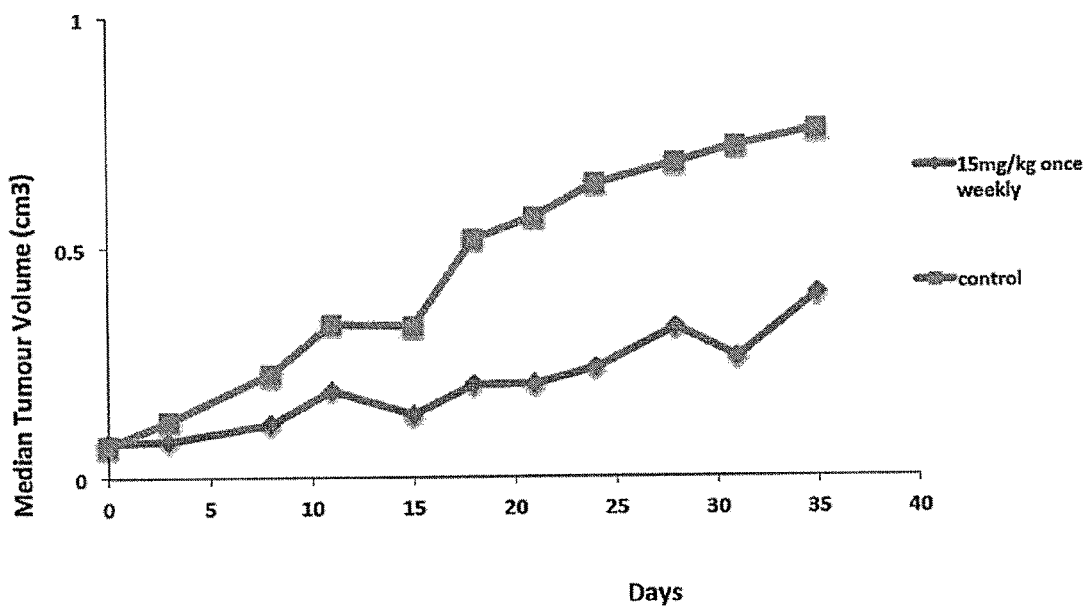
FIG. 5 shows the median tumour volume of a control group of mice compared to a group of mice given 3d at 15 mg/kg once weekly.

In a subsequent experiment using CD1 nu/nu female mice as described above, mice were allocated into groups (six mice per group) as follows: control group (IV 100 uL/10 g sterile PBS) and 3d at 15 mg/kg given once weekly. The observations finished when tumours reached a size of 1 cm$^3$ or when mice showed weight loss of up to 20%. Mice given 3d at 15 mg/kg once weekly gave a sustained antitumour response (see FIG. 5). In the control group the median time to endpoint was 42 days compared to 79 days in the treated group. Of the six mice in the treated group, two had a complete response and remained tumour free at 136 days. The therapy was well tolerated under this schedule.

Figure 6:
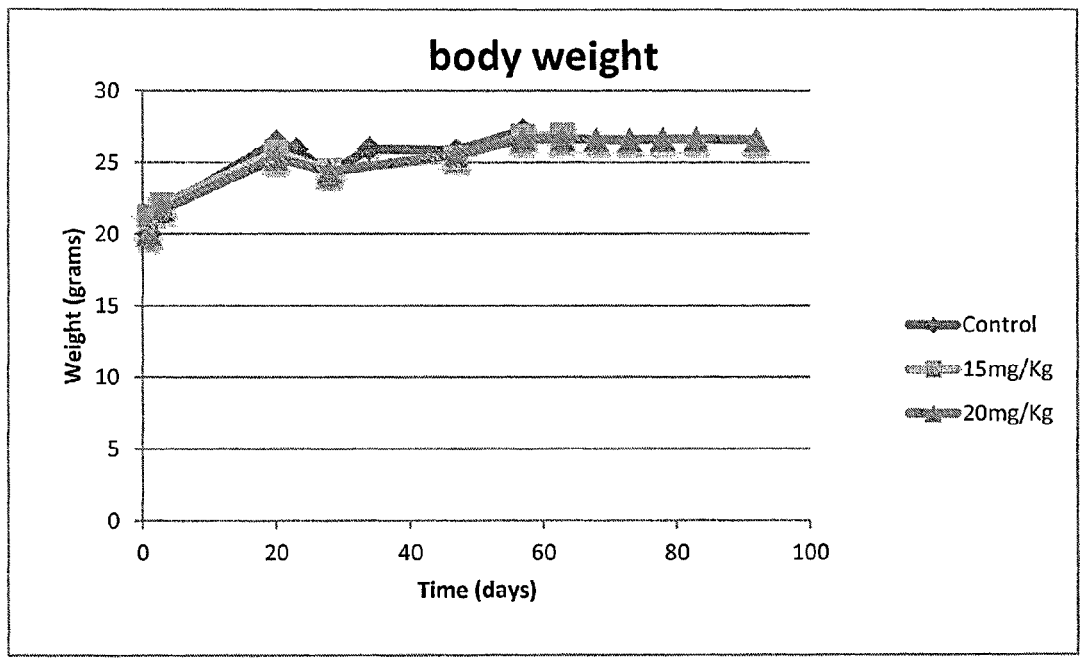
FIG. 6 shows the body weight of a control group of mice compared to a group of mice given a single dose of 3d at 20 mg/kg and a group of mice given 3d at 15 mg/kg once weekly.

Overall the data shows clear evidence of in vivo anticancer activity without any significant bodyweight loss. FIG. 6 shows the body weight of a control group of mice compared to a group of mice given a single dose of 3d at 20 mg/kg and a group of mice given 3d at 15 mg/kg once weekly.

DISCUSSION

The tetra-substituted naphthalene diimides reported here show anti-proliferative activity in the cancer cell line panel used here. The activity of the dicationic compounds 3b, 3c and 3e is unlikely to involve telomere maintenance disruption via the stabilization of human telomeric quadruplex DNA, in view of their low level of quadruplex binding, as found in the in vitro FRET assay.

The prediction from the crystal structures, that the bis-morpholine compound 3d would have quadruplex stabilizing ability comparable to that of the previously-described compound 4, is borne out by the FRET data. It can be concluded therefore that the data obtained on the morpholine modified compounds supports the rationale of this study. The slight decrease in $\Delta T_m$ value for the quadruplex complex with 3d, compared to the behaviour of compound 4, is consistent with the reduced basicity of the morpholino group, leading to a reduced electrostatic contribution to stabilization. A key requirement of small molecules in order to demonstrate high-affinity quadruplex binding (accompanied by biological activity), has generally been accepted as the possession of cationic groups, most commonly attached to flexible side-chains. The data on compound 3d (and 3h) show that side-chain basicity can be modulated without significant deleterious effects on ability to bind to human telomeric quadruplex DNA, yet with significant changes in biological profile.

The profiles of potency in cell growth inhibition shown by compounds 3d and the shorter chain-length compound 3h in a panel of cancer cell lines are superior to that of compound 4, consistent with the prediction of improved pharmacological properties for the former. It is notable that in common with compound 4, both dimorpholine compounds 3d and 3h show selectivity for some of these cancer cell lines when compared to the normal fibroblast line WI-38. Selectivity was found to be greatest for the pancreatic Mia-PaCa2 cell line, ~20-fold for 3d and ~200-fold for 3h, suggesting that these compounds could have a useable therapeutic window in vivo—this is borne out by very recent tumour xenograft experiments with 3d showing significant activity in the Mia-PaCa2 pancreatic tumour xenograft model (J A Hartley et al., to be published). The cellular selectivity and possible therapeutic window does not appear to be directly related to the slightly greater stabilization of duplex DNA shown by the morpholine compounds compared to compound 4. The lack of significant quadruplex binding shown by the furan, tetrahydrofuran and methoxy-containing compounds, suggests that the ability to participate in hydrogen-bonding in the quadruplex grooves as observed in the crystal structures in this series, is a requirement for all four end-groups in these ND compounds.

Mia-PaCa2 carcinoma cells are well-established to be telomerase-positive and telomere-maintenance defective; the present results support the concept that the two effects can be separated, at least in this pancreatic cancer cell line. Remarkably, compounds 3d and 3h are not inhibitors of telomerase activity, at least at the doses relevant to the IC$_{50}$ values reported here, in striking contrast to the finding that symmetrically tetra-substituted naphthalene diimides such as compound 4, invoke DNA damage responses closely analogous to those found for a number of other telomeric quadruplex ligands, such as the appearance of γ-H2AX foci. By contrast the morpholine compounds 3d and 3h do not appear to induce these particular changes. This is consistent with the pattern of transcriptional changes in DNA damage response genes (FIG. 3), which indicates that the ATM/ATR pathways are not activated, but instead genes encoding a number of other markers of cellular stress and the DNA damage response are up-regulated—notably the GADD45A and GADD45G, DDIT3 and CDKN1A genes. DDIT3 has been shown to act as a dominant negative transcriptional regulator, mediating G1 cell cycle arrest in response to DNA damage, ER stress, hypoxia, and starvation and has also been linked to apoptosis in certain cell types. CDKN1A encodes the p21WAF1 protein, which mediates cell growth arrest and senescence. The strong induction of this gene is consistent with the morphological observation of a pronounced increase in senescence in 3d-treated Mia-PaCa2 cells (FIG. 9).

The qPCR expression data is suggestive of cell cycle checkpoint arrest that is not purely mediated by changes in telomere organisation, although the moderate changes in the expression levels of several telomere-associated genes is consistent with their involvement in the arrest of cancer cell growth. It is also notable that expression of the PARP (poly (ADP-ribose) polymerase) gene is down-regulated; the PARP protein is involved in the repair of single-strand breaks and its inhibition by small molecules is currently the subject of clinical trials in several cancers. The dose-dependent down-regulation of PARP expression observed here may thus contribute to the overall anti-proliferative effects of compound 3d and to its anticancer effects in vivo.

ABBREVIATIONS USED

OAc, acetyl; FRET, Fluorescence Resonance Energy Transfer; HTel, human telomeric DNA; TRAP, Telomerase Repeat Amplification Protocol; CT, calf thymus; MR, molecular replacement; ND, naphthalene diimide; NMP, N-methylpyrrolidinone.

REFERENCES

1. Gunaratnam, M.; Swank, S.; Haider, S. M.; Galesa, K.; Reszka, A. P.; Beltran, M.; Cuenca, F.; Fletcher, J. A.; Neidle, S. Targeting human gastrointestinal stromal tumour cells with a quadruplex-binding small molecule. *J. Med. Chem.* 2009, 52, 3774-3783.
2. Hampel, S. M.; Sidibe, A.; Gunaratnam, M.; Riou, J.-F.; Neidle, S. Tetrasubstituted naphthalene diimide ligands with selectivity for telomeric G-quadruplexes and cancer cells. *Bioorg. Med. Chem. Lett.* 2010, 20, 6459-6463.
3. Gunaratnam, M.; de la Fuente, M.; Hampel, S. M.; Todd, A. K.; Reszka, A. P.; Schatzlein, A.; Neidle, S. Targeting pancreatic cancer with a G-quadruplex ligand. *Bioorg. Med. Chem.* 2011, 19, 7151-7157.
4. Chaignon, F.; Falkenström, M.; Karlsson, S.; Blart, E.; Odobel, F.; Hammarström, L., Very large acceleration of the photoinduced electron transfer in a Ru(bpy)$_3$-naphthalene bisimide dyad bridged on the naphthyl core. *Chem. Comm.* 2007, 7, 64-66.
5. Lu, X.; Zhu, W.; Xie, Y.; Li, X.; Gao, Y.; Li, F.; Tian, H., Near-IR core-substituted naphthalenediimide fluorescent chemosensors for zinc ions: ligand effects on PET and ICT channels. *Chem. Eur. J.* 2010, 16, 8355-8364.

What is claimed is:

1. A compound of general formula (I) or a pharmaceutically acceptable salt or prodrug thereof

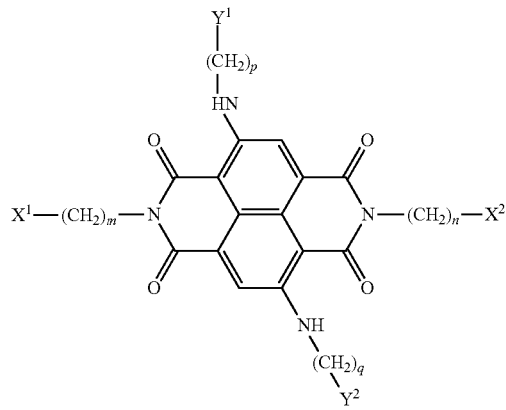

(I)

wherein m, n, p and q are each independently selected from integers 2 or 3; and wherein $X^1$ and $X^2$ are N-methyl piperazine and $Y^1$ and $Y^2$ are morpholino or $X^1$ and $X^2$ are morpholino and $Y^1$ and $Y^2$ are N-methyl piperazine.

2. A compound according to claim 1, wherein $X^1$ and $X^2$ are N-methyl piperazine.

3. A compound according to claim 1, wherein $Y^1$ and $Y^2$ are morpholino.

4. A compound according to claim 3, wherein p and q are both 2.

5. A compound according to claim 1, wherein $X^1$ and $X^2$ are N-methyl piperazine; wherein $Y^1$ and $Y^2$ are morpholino; and wherein p and q are independently selected from integers 2 or 3.

6. A compound according to claim 1, selected from the following compounds:

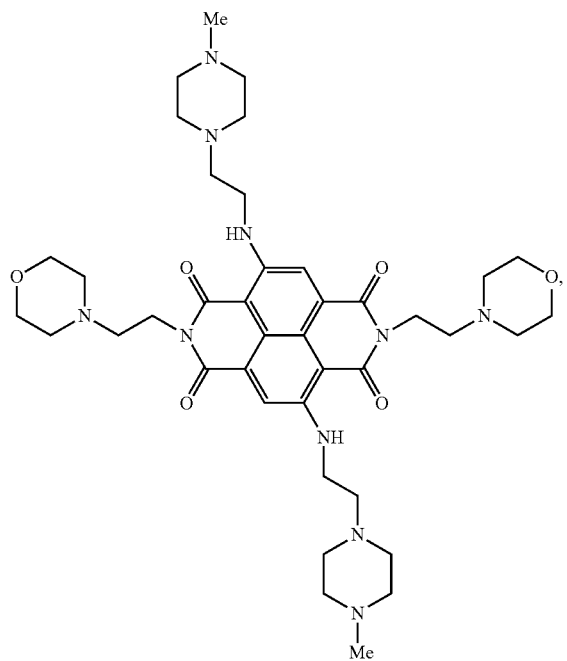

3g

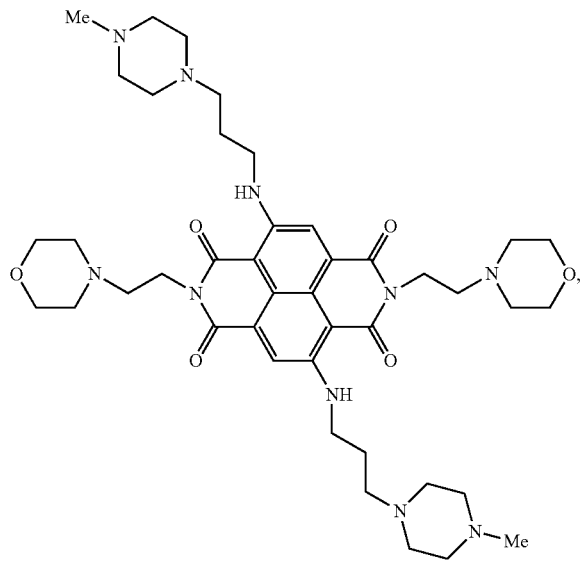

3f

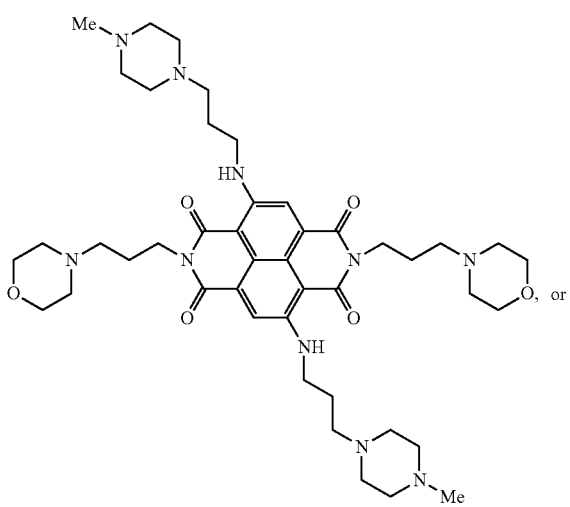

3d

, or

3h

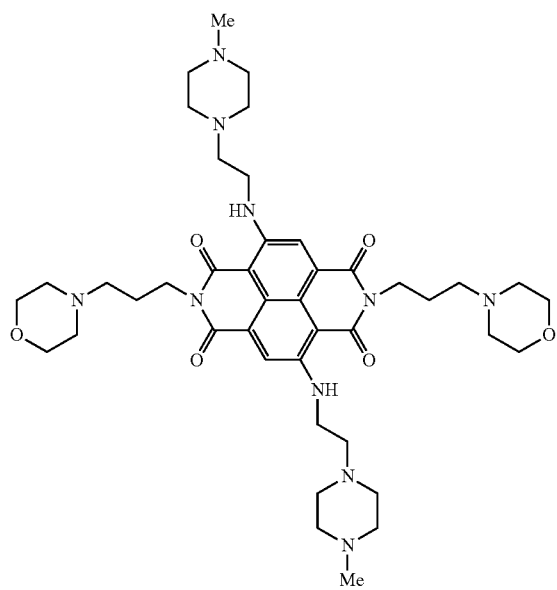

7. A method for the treatment of cancer comprising administering to a subject a compound according to claim 1, or a salt, solvate or prodrug thereof, wherein the cancer is lung cancer, renal cancer, pancreatic cancer or breast cancer.

8. A method according to claim 7, wherein $X^1$ and $X^2$ are N-methyl piperazine.

9. A method according to claim 7, wherein $Y^1$ and $Y^2$ are morpholino.

10. A method of preparation of a pharmaceutical composition, the method comprising: obtaining a compound according to claim 1, and combining the compound with a pharmaceutically acceptable carrier.

11. A method according to claim 10, wherein $X^1$ and $X^2$ are N-methyl piperazine.

12. A method according to claim 10, wherein $Y^1$ and $Y^2$ are morpholino.

13. A pharmaceutical composition comprising a compound according to claim 1.

14. A pharmaceutical composition according to claim 13, wherein $X^1$ and $X^2$ are N-methyl piperazine.

15. A pharmaceutical composition according to claim 13, wherein $Y^1$ and $Y^2$ are morpholino.

16. A compound or a pharmaceutically acceptable salt or prodrug thereof of the formula:

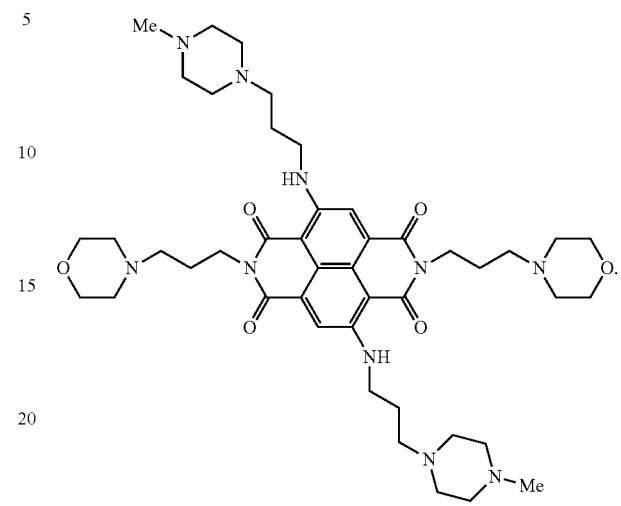

17. A compound or a pharmaceutically acceptable salt or prodrug thereof of the formula:

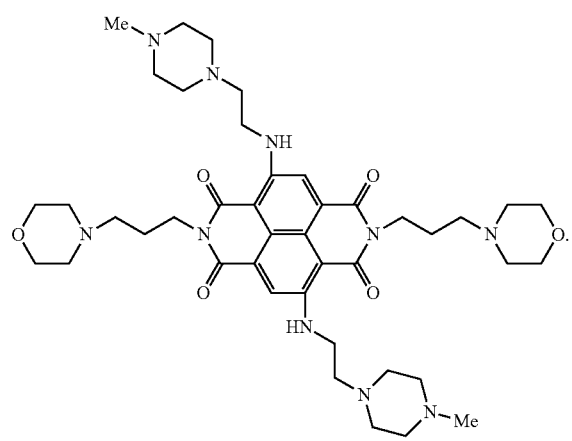 [SMILES: CN1CCN(CCNc2cc3c4c(c(NCCN5CCN(C)CC5)cc5c4c2C(=O)N(CCCN2CCOCC2)C5=O)C(=O)N(CCCN2CCOCC2)C3=O)CC1]

* * * * *